United States Patent
Ishida et al.

(10) Patent No.: US 8,828,429 B2
(45) Date of Patent: Sep. 9, 2014

(54) RELEASE-CONTROL COMPOSITION

(75) Inventors: Hajime Ishida, Osaka (JP); Yukihiro Nomura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1686 days.

(21) Appl. No.: 11/885,467

(22) PCT Filed: Mar. 3, 2006

(86) PCT No.: PCT/JP2006/304672
§ 371 (c)(1),
(2), (4) Date: May 30, 2008

(87) PCT Pub. No.: WO2006/093353
PCT Pub. Date: Sep. 8, 2006

(65) Prior Publication Data
US 2009/0053308 A1 Feb. 26, 2009

(30) Foreign Application Priority Data

Mar. 3, 2005 (JP) .................................. 2005-059501

(51) Int. Cl.
| A61K 9/62 | (2006.01) |
| A61K 9/60 | (2006.01) |
| A61K 9/50 | (2006.01) |
| A61K 9/58 | (2006.01) |
| A61K 31/415 | (2006.01) |
| A61K 31/4188 | (2006.01) |
| A61K 9/48 | (2006.01) |

(52) U.S. Cl.
CPC ............ *A61K 9/5078* (2013.01); *A61K 9/5042* (2013.01); *A61K 9/4866* (2013.01); *A61K 31/4188* (2013.01); *A61K 9/5026* (2013.01)
USPC ........... 424/461; 424/459; 424/497; 424/462; 514/393

(58) Field of Classification Search
USPC .................... 424/461, 459, 497, 462; 514/393
See application file for complete search history.

(56) References Cited

U.S. PATENT DOCUMENTS

| 5,994,395 A * | 11/1999 | Lowndes et al. ............... 514/460 |
| 6,861,071 B2 | 3/2005 | Kataoka et al. |
| 2005/0043544 A1 | 2/2005 | Nuwa et al. |
| 2006/0013868 A1 | 1/2006 | Akiyama et al. |
| 2006/0177506 A1 | 8/2006 | Yanai et al. |

FOREIGN PATENT DOCUMENTS

| EP | 0 356 673 | 3/1990 |
| EP | 0 426 225 | 5/1991 |
| EP | 1 471 056 | 10/2004 |
| EP | 1 477 161 | 11/2004 |
| EP | 1 607 092 | 12/2005 |
| JP | 2002-193831 | 7/2002 |
| JP | 2004-161653 | 6/2004 |
| JP | 2004-300148 | 10/2004 |
| WO | WO-93/15079 | 8/1993 |
| WO | WO 02/11726 A1 | 2/2002 |
| WO | WO 02/40484 A2 | 5/2002 |
| WO | WO 03/059889 A1 | 7/2003 |
| WO | WO 2004/035024 A1 | 4/2004 |
| WO | WO 2004/075890 A1 | 9/2004 |
| WO | WO 2004/082679 A1 | 9/2004 |
| WO | WO 2007/074856 A1 | 7/2007 |

OTHER PUBLICATIONS

Data sheet for CELPHERE TM Microcystalline cellulose spherical seed core data sheet by Asahi Kasei (2004, pp. 1-2).*
Zips et al. In vivo 2005, 19, 1-8.*
Sikora: Current Science 2001, 81(5), 549-554.*
Supplemental European Search Report mailed Feb. 22, 2011 in corresponding European Patent Application 06715493.0.
International Search Report for PCT/JP2006/304672, Jun. 6, 2006.

* cited by examiner

*Primary Examiner* — Aradhana Sasan
(74) *Attorney, Agent, or Firm* — Edwards Wildman Palmer LLP; David G. Conlin; Mark D. Russett

(57) ABSTRACT

The present invention relates to a controlled release capsule preparation for oral administration, which contains (i) a granule containing a physiologically active substance which is a compound represented by the formula:

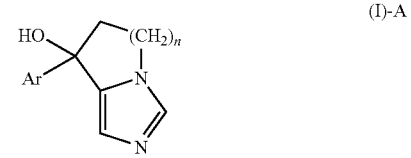

(I)-A wherein n is an integer of 1 to 3, and Ar is an aromatic ring optionally having substituent(s), or a salt thereof, and a hydrophilic polymer, and coated with an enteric coating agent and the like, and (ii) a fluidizer. According to the present invention, a controlled release composition for oral administration of an imidazole derivative, which has steroid $C_{17,20}$-lyase inhibiting activity and which has remarkably improved sustainability of the blood concentration, is provided.

1 Claim, No Drawings

RELEASE-CONTROL COMPOSITION

CROSS-REFERENCE TO RELATED APPLICATIONS

This application is the 35 U.S.C. §371 national stage of PCT application PCT/JP2006/304672, filed Mar. 3, 2006, which claims priority to Japanese patent application No. 059501/2005, filed Mar. 3, 2005. The contents of these applications are incorporated herein by reference in their entirety.

TECHNICAL FIELD

The present invention relates to a controlled release composition. More specifically, the invention relates to a controlled release capsule preparation for oral administration comprising (i) a granule containing a steroid $C_{17,20}$-lyase inhibiting substance which exhibits high water solubility under acidic conditions and a hydrophilic polymer, which is coated with an enteric coating agent and (ii) a fluidizer, more specifically, a controlled release capsule preparation for oral administration comprising (i) an enteric granule wherein a core particle is coated with the steroid $C_{17,20}$-lyase inhibiting substance and a hydrophilic polymer to form a plain granule which is then coated with an enteric coating agent and (ii) a fluidizer.

BACKGROUND ART

Preparations for oral administration such as tablets, capsules and granules can be easily administered and are safe as compared with injections or the like, thus being the most frequently used dosage forms in the medical field. In recent years, under the purpose of improving a patient's QOL (Quality of Life) and providing medical care in an energy-saving and economic way, preparations for oral administration which maintain the effect for a long time with once or twice a day administration have been developed.

Since a drug having high water solubility under acidic conditions is such that when formulated into a general immediate release preparation, it is rapidly dissolved out in the stomach and absorbed, the duration of the effective blood concentration is short. Further, there are problems such as expression of toxicity due to a sharp rise in the initial blood concentration of the drug. Therefore, it is strongly desirable to develop a controlled release preparation which is imparted with, in particular, the property of sustained release or non-release in the stomach. However, in many cases, the in vivo pharmacokinetics in blood may not be exhibited in the same way as expected from an in vitro dissolution test, and there still exist a large number of drugs which have not yet been formulated into effective controlled release preparations for oral administration.

WO 02/40484 discloses a steroid $C_{17,20}$-lyase inhibiting substance having a superior anticancer action.

WO 2004/82679 discloses a controlled release composition containing the above-mentioned steroid $C_{17,20}$-lyase inhibiting substance and a hydrophilic polymer.

DISCLOSURE OF THE INVENTION

An object of the present invention is to provide a controlled release composition for oral administration, wherein the sustainability of the effective blood concentration of the above-mentioned steroid $C_{17,20}$-lyase inhibiting substance is further improved.

The present inventors have conducted intensive investigations in order to achieve the above-described object and, as a result, found that the maximum blood concentration can be remarkably lowered as compared to an immediate-release preparation and a sustained drug release can be realized for a long time thereafter when granules containing the above-mentioned steroid $C_{17,20}$-lyase inhibiting substance and a hydrophilic polymer, which is coated with an enteric coating agent, and a fluidizer are concurrently enclosed in a capsule. The inventors have conducted further research based on these findings, and have completed the invention.

That is, the present invention provides:

[1] a controlled release capsule preparation for oral administration, which comprises (i) a granule comprising a physiologically active substance, which is a compound represented by the formula:

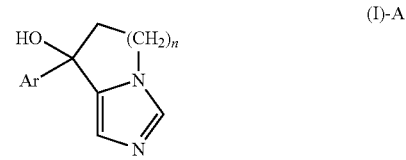

(I)-A wherein n is an integer of 1 to 3, and Ar is an aromatic ring optionally having substituent(s), or a salt thereof, and a hydrophilic polymer, wherein the granule is coated with a coating layer comprising an enteric coating agent, and (ii) a fluidizer,

[2] a controlled release capsule preparation for oral administration, which comprises (i) an enteric granule comprising a plain granule wherein a core particle is coated with a coating layer comprising a physiologically active substance, which is a compound represented by the formula:

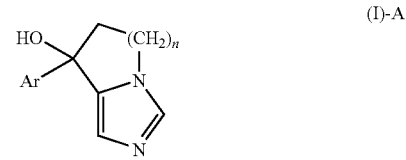

(I)-A wherein n is an integer of 1 to 3, and Ar is an aromatic ring optionally having substituent(s), or a salt thereof, and a hydrophilic polymer, wherein the plain granule is coated with a coating layer comprising an enteric coating agent, and (ii) a fluidizer,

[3] the controlled release capsule preparation for oral administration of the above-mentioned [1] or [2], which has the following dissolution characteristics:
1) in Method 1 of the dissolution test in the Japanese Pharmacopoeia (rotating basket method, rotation speed 125 rpm, 37° C.) using 1000 mL of 0.1 mol/L hydrochloric acid, the dissolution rate of a physiologically active substance from a controlled release capsule preparation at 120 min after the start of the test is less than 10%, preferably less than 5%, more preferably less than 3%, and
2) in Method 1 of the dissolution test in the Japanese Pharmacopoeia (rotating basket method, rotation speed 125 rpm, 37° C.) using a phosphate buffer (pH 7.2, 1000 mL) containing sodium dodecyl sulfate at 0.5%, the dissolution rate of a physiologically active substance from a controlled release capsule preparation at 45 min after the start of the test is not less than 70%, preferably not less than 80%, more preferably not less than 90%,

[4] a controlled release capsule preparation for oral administration of the above-mentioned [1], which comprises (i) a granule comprising (1) a physiologically active substance, which is a compound represented by the formula:

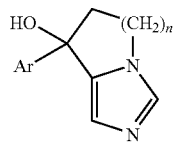

(I)-A wherein n is an integer of 1 to 3, and Ar is an aromatic ring optionally having substituent(s), or a salt thereof, and
(2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose, wherein the granule is coated with a coating layer comprising (3) an enteric coating agent selected from the group consisting of cellulose acetate phthalate, hydroxypropylmethylcellulose phthalate, hydroxymethylcellulose acetate succinate and methacrylic acid copolymers, and
(ii) a fluidizer selected from the group consisting of light anhydrous silicic acid, hydrated silicon dioxide, microcrystalline cellulose, synthetic aluminum silicate, titanium oxide, heavy anhydrous silicic acid, magnesium hydroxide-aluminum hydroxide co-precipitate, stearic acid, magnesium stearate, calcium stearate, tribasic calcium phosphate, talc, corn starch, magnesium aluminometasilicate and dibasic calcium phosphate fine granulated product,

[5] the controlled release capsule preparation for oral administration of the above-mentioned [2], which comprises (i) an enteric granule comprising a plain granule wherein a core particle is coated with a coating layer comprising (1) a physiologically active substance, which is a compound represented by the formula:

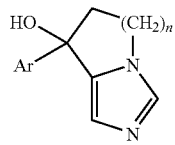

(I)-A wherein n is an integer of 1 to 3, and Ar is an aromatic ring optionally having substituent(s), or a salt thereof and
(2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose, wherein the plain granule is coated with a coating layer comprising
(3) an enteric coating agent selected from the group consisting of cellulose acetate phthalate, hydroxypropylmethylcellulose phthalate, hydroxymethylcellulose acetate succinate and methacrylic acid copolymers, and
(ii) a fluidizer selected from the group consisting of light anhydrous silicic acid, hydrated silicon dioxide, microcrystalline cellulose, synthetic aluminum silicate, titanium oxide, heavy anhydrous silicic acid, magnesium hydroxide-aluminum hydroxide co-precipitate, stearic acid, magnesium stearate, calcium stearate, tribasic calcium phosphate, talc, corn starch, magnesium aluminometasilicate and dibasic calcium phosphate fine granulated product,

[6] the controlled release capsule preparation for oral administration of the above-mentioned [2], which comprises (i) an enteric granule comprising a plain granule wherein a core particle is coated with a coating layer comprising (1) a physiologically active substance, which is a compound represented by the formula:

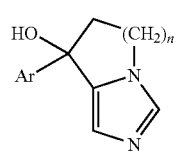

(I)-A wherein n is an integer of 1 to 3, and Ar is an aromatic ring optionally having substituent(s), or a salt thereof,
(2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose,
(3) an excipient selected from the group consisting of lactose, sucrose, D-mannitol, D-sorbitol, starch, pregelatinized starch, dextrin, microcrystalline cellulose, low-substituted hydroxypropylcellulose, sodium carboxymethylcellulose, gum arabic, dextrin, pullulan, synthetic aluminum silicate and magnesium aluminometasilicate, and
(4) a disintegrant selected from the group consisting of lactose, sucrose, starch, carboxymethylcellulose, calcium carboxymethylcellulose, croscarmellose sodium, microcrystalline cellulose, sodium carboxymethyl starch and low-substituted hydroxypropylcellulose, wherein the plain granule is coated with a coating layer comprising
(5) (a) an enteric coating agent selected from the group consisting of cellulose acetate phthalate, hydroxypropylmethylcellulose phthalate, hydroxymethylcellulose acetate succinate and methacrylic acid copolymers,
(b) a lubricant selected from the group consisting of magnesium stearate, calcium stearate, talc, colloidal silica, synthetic aluminum silicate and magnesium aluminometasilicate, and
(c) a plasticizer selected from the group consisting of acetyl tributyl citrate, acetyl triethyl citrate, castor oil, diacetylated monoglyceride, dibutyl sebacate, diethyl phthalate, glycerin, mono- and diacetylated monoglyceride, polyethylene glycol, propylene glycol, triacetin and triethyl citrate,
(ii) a fluidizer selected from the group consisting of light anhydrous silicic acid, hydrated silicon dioxide, microcrystalline cellulose, synthesis aluminum silicate, titanium oxide, heavy anhydrous silicic acid, magnesium hydroxide-aluminum hydroxide co-precipitate, stearic acid, magnesium stearate, calcium stearate, tribasic calcium phosphate, talc, corn starch, magnesium alumino metasilicate and dibasic calcium phosphate fine granulated product, and
(iii) a lubricant selected from the group consisting of magnesium stearate, calcium stearate, talc, colloidal silica, synthetic aluminum silicate and magnesium aluminometasilicate,

[7] the controlled release capsule preparation for oral administration of any one of the above-mentioned [1] to [6], wherein the physiologically active substance is (+)-6-(7-hydroxy-6,7-dihydro-5H-pyrrolo[1,2-c]imidazol-7-yl)-N-methyl-2-naphthamide or a salt thereof,

[8] the controlled release capsule preparation for oral administration of any one of the above-mentioned [1] to [6], wherein the fluidizer is light anhydrous silicic acid,

[9] the controlled release capsule preparation for oral administration of any one of the above-mentioned [2], [3], [5] and [6], wherein the core particle is a particle selected from the group consisting to microcrystalline cellulose, sucrose, lactose, starch and waxes,

[10] the controlled release capsule preparation for oral administration of any one of the above-mentioned [2], [3], [5] and [6], wherein the core particle is a microcrystalline cellulose particle,

[11] the controlled release capsule preparation for oral administration of any one of the above-mentioned [1] to [10], which is used for the prophylaxis or treatment of cancer,

[12] the controlled release capsule preparation for oral administration of any one of the above-mentioned [1] to [10], which is used for the prophylaxis or treatment of prostate cancer or breast cancer,

[13] a method of producing a granule comprising coating a core particle with a coating agent comprising (1) a physiologically active substance, which is a compound represented by the formula:

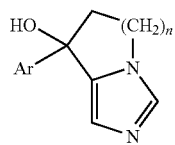

(I)-A wherein n is an integer of 1 to 3, and Ar is an aromatic ring optionally having substituent(s), or a salt thereof, and (2) a hydrophilic polymer (e.g., a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose) using a rotating blade fluidizing granulator, wherein the following conditions are set;

(i) adhesion to a nozzle of the rotating blade fluidizing granulator is prevented, (ii) drying conditions: inlet air temperature is 55 to 75° C., preferably 60 to 70° C., and inlet air flow is 1.0 to 3.0 m$^3$/min, preferably 1.5 to 2.5 m$^3$/min, per 3.5 L of effective capacity of the rotating blade fluidizing granulator, (iii) temperature conditions: product temperature is 25 to 35° C., preferably 25 to 30° C., (iv) humidity conditions: exhaustion humidity is 60 to 95% RH, preferably 60 to 90% RH, more preferably 70 to 80% RH, and (v) spray rate: spray rate is 20 to 40 g/min, preferably 25 to 35 g/min, per 3.5 L of effective capacity of the rotating blade fluidizing granulator,

[14] a granule wherein a core particle is coated with a coating layer comprising (1) a physiologically active substance, which is a compound represented by the formula:

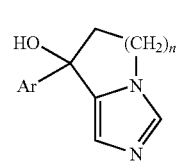

(I)-A wherein n is an integer of 1 to 3, and Ar is an aromatic ring optionally having substituent(s), or a salt thereof and (2) a hydrophilic polymer (e.g., a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose), which is produced by the production method of the above-mentioned [13],

[15] a pharmaceutical composition comprising the granule of the above-mentioned [14],

[16] the pharmaceutical composition of the above-mentioned [15], which is an agent for the prophylaxis or treatment of prostate cancer, breast cancer, uterine cancer or ovarian cancer,

[17] a method for the prophylaxis or treatment of prostate cancer, breast cancer, uterine cancer or ovarian cancer, which comprises administering an effective amount of the pharmaceutical composition of the above-mentioned [15] to a mammal,

[18] use of the pharmaceutical composition of the above-mentioned [15] for the production of an agent for the prophylaxis or treatment of prostate cancer, breast cancer, uterine cancer or ovarian cancer,

[19] a method of producing a granule comprising coating a core particle with a coating agent comprising a physiologically active substance and a disintegrant using a rotating blade fluidizing granulator, wherein the following conditions are set;

(i) humidity conditions: exhaustion humidity is 60 to 95% RH, and (ii) the disintegrant is croscarmellose sodium or microcrystalline cellulose,

[20] the production method of the above-mentioned [19], wherein the following conditions are set;

(i) adhesion to a nozzle of the rotating blade fluidizing granulator is prevented, (ii) drying conditions: inlet air temperature is 55 to 75° C., and inlet air flow is 1.0 to 3.0 m$^3$/min per 3.5 L of effective capacity of the rotating blade fluidizing granulator, (iii) temperature conditions: product temperature is 25 to 35° C., (iv) humidity conditions: exhaustion humidity is 60 to 95% RH, (v) spray rate: spray rate is 20 to 40 g/min per 3.5 L of effective capacity of the rotating blade fluidizing granulator, and (vi) the disintegrant is croscarmellose sodium or microcrystalline cellulose,

[21] the production method of the above-mentioned [19] or [20], wherein the coating agent further comprises a hydrophilic polymer and (or) an excipient besides the physiologically active substance and the disintegrant,

[22] a granule wherein a core particle is coated with a coating layer comprising a physiologically active substance and a disintegrant, which is produced by the production method of the above-mentioned [19],

[23] a pharmaceutical composition comprising the granule of the above-mentioned [22],

[24] the pharmaceutical composition of the above-mentioned [23], which is a controlled release capsule preparation for oral administration,

[25] a controlled release capsule preparation for oral administration, which comprises (i) a granule comprising a physiologically active substance, which is a compound represented by the formula:

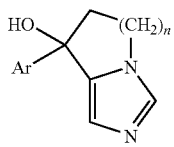

(I)-A wherein n is an integer of 1 to 3, and Ar is an aromatic ring optionally having substituent(s), or a salt thereof, and a hydrophilic polymer, wherein the granule is coated with an enteric coating agent, and (ii) a fluidizer,

[26] a controlled release capsule preparation for oral administration, which comprises (i) an enteric granule comprising a plain granule wherein a core particle is coated with a physiologically active substance, which is a compound represented by the formula:

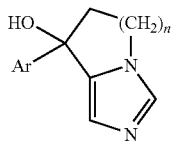

(I)-A wherein n is an integer of 1 to 3, and Ar is an aromatic ring optionally having substituent(s), or a salt thereof and a hydrophilic polymer, wherein the granule is coated with an enteric coating agent, and (ii) a fluidizer,

[27] the controlled release composition of the above-mentioned [25] or [26], which has the following elution characteristics:

1) in Method 1 of the dissolution test in the Japanese Pharmacopoeia (rotating basket method, rotation speed 125 rpm, 37° C.) using 1000 mL of 0.1 mol/L hydrochloric acid, the dissolution rate of a physiologically active substance from a controlled release composition at 120 min after the start of the test is less than 10%, preferably less than 5%, more preferably less than 3%, and 2) in Method 1 of the dissolution test in the Japanese Pharmacopoeia (rotating basket method, rotation speed 125 rpm, 37° C.) using a phosphate buffer (pH 7.2, 1000 mL) containing sodium dodecyl sulfate at 0.5%, the dissolution rate of a physiologically active substance from a controlled release composition at 45 min after the start of the test is not less than 70%, preferably not less than 80%, more preferably not less than 90%,

[28] the controlled release capsule preparation for oral administration of the above-mentioned [25], which comprises (i) a granule comprising (1) a physiologically active substance, which is a compound represented by the formula:

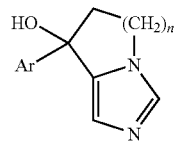

(I)-A wherein n is an integer of 1 to 3, and Ar is an aromatic ring optionally having substituent(s), or a salt thereof and
(2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose, wherein the granule is coated with
(3) an enteric coating agent selected from the group consisting of cellulose acetate phthalate, hydroxypropylmethylcellulose phthalate, hydroxymethylcellulose acetate succinate and methacrylic acid copolymers,
(ii) a fluidizer selected from the group consisting of light anhydrous silicic acid, hydrated silicon dioxide, microcrystalline cellulose, synthesis aluminum silicate, titanium oxide, heavy anhydrous silicic acid, magnesium hydroxide-aluminum hydroxide co-precipitate, stearic acid, magnesium stearate, calcium stearate, tribasic calcium phosphate, talc, corn starch, magnesium alumino metasilicate and dibasic calcium phosphate fine granulated product,

[29] the controlled release capsule preparation for oral administration of the above-mentioned [26], which comprises (i) an enteric granule comprising a plain granule wherein a core particle is coated with (1) a physiologically active substance, which is a compound represented by the formula:

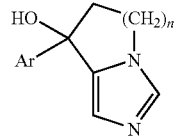

(I)-A wherein n is an integer of 1 to 3, and Ar is an aromatic ring optionally having substituent(s), or a salt thereof and
(2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose, wherein the plain granule is coated with
(3) an enteric coating agent selected from the group consisting of cellulose acetate phthalate, hydroxypropylmethylcellulose phthalate, hydroxymethylcellulose acetate succinate and methacrylic acid copolymers, and
(ii) a fluidizer selected from the group consisting of light anhydrous silicic acid, hydrated silicon dioxide, microcrystalline cellulose, synthetic aluminum silicate, titanium oxide, heavy anhydrous silicic acid, magnesium hydroxide-aluminum hydroxide co-precipitate, stearic acid, magnesium stearate, calcium stearate, tribasic calcium phosphate, talc, corn starch, magnesium aluminometasilicate and dibasic calcium phosphate fine granulated product,

[30] the controlled release capsule preparation for oral administration of the above-mentioned [26], which comprises (i) an enteric granule comprising a plain granule wherein a core particle is coated with (1) a physiologically active substance, which is a compound represented by the formula:

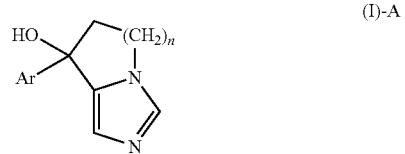

wherein n is an integer of 1 to 3, and Ar is an aromatic ring optionally having substituent(s), or a salt thereof,
(2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose,
(3) an excipient selected from the group consisting of lactose, sucrose, D-mannitol, D-sorbitol, starch, pregelatinized starch, dextrin, microcrystalline cellulose, low-substituted hydroxypropylcellulose, sodium carboxymethylcellulose, gum arabic, dextrin, pullulan, synthetic aluminum silicate and magnesium aluminometasilicate, and
(4) a disintegrant selected from the group consisting of lactose, sucrose, starch, carboxymethylcellulose, calcium carboxymethylcellulose, croscarmellose sodium, microcrystalline cellulose, sodium carboxymethyl starch and low-substituted hydroxypropylcellulose, wherein the plain granule is coated with a coating agent comprising
(5) (a) an enteric coating agent selected from the group consisting of cellulose acetate phthalate, hydroxypropylmethylcellulose phthalate, hydroxymethylcellulose acetate succinate and methacrylic acid copolymers,
(b) a lubricant selected from the group consisting of magnesium stearate, calcium stearate, talc, colloidal silica, synthetic aluminum silicate and magnesium aluminometasilicate, and
(c) a plasticizer selected from the group consisting of acetyl tributyl citrate, acetyl triethyl citrate, castor oil, diacetylated monoglyceride, dibutyl sebacate, diethyl phthalate, glycerin, mono- and diacetylated monoglyceride, polyethylene glycol, propylene glycol, triacetin and triethyl citrate,
(ii) a fluidizer selected from the group consisting of light anhydrous silicic acid, hydrated silicon dioxide, microcrystalline cellulose, synthesis aluminum silicate, titanium oxide, heavy anhydrous silicic acid, magnesium hydroxide-aluminum hydroxide co-precipitate, stearic acid, magnesium stearate, calcium stearate, tribasic calcium phosphate, talc, corn starch, magnesium alumino metasilicate and dibasic calcium phosphate fine granulated product, and
(iii) a lubricant selected from the group consisting of magnesium stearate, calcium stearate, talc, colloidal silica, synthetic aluminum silicate and magnesium aluminometasilicate,
[31] the controlled release capsule preparation for oral administration of any one of the above-mentioned [25] to [30], wherein the physiologically active substance is (+)-6-(7-hydroxy-6,7-dihydro-5H-pyrrolo[1,2-c]imidazol-7-yl)-N-methyl-2-naphthamide or a salt thereof,
[32] the controlled release capsule preparation for oral administration of any one of the above-mentioned [25] to [30], wherein the fluidizer is light anhydrous silicic acid,
[33] the controlled release capsule preparation for oral administration of any one of the above-mentioned [25] to [32], wherein the core particle is a particle selected from the group consisting of microcrystalline cellulose, sucrose, lactose, starch and waxes,
[34] the controlled release capsule preparation for oral administration of any one of the above-mentioned [25] to [32], wherein the core particle is a microcrystalline cellulose particle,
[35] the controlled release capsule preparation for oral administration of any one of the above-mentioned [25] to [34], which is used for the prophylaxis or treatment of cancer,
[36] the controlled release capsule preparation for oral administration of any one of the above-mentioned [25] to [34], which is used for the prophylaxis or treatment of prostate cancer or breast cancer,
[37] a method of producing a granule comprising coating a core particle with (1) a physiologically active substance, which is a compound represented by the formula:

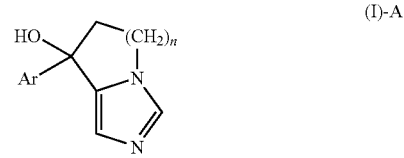

wherein n is an integer of 1 to 3, and Ar is an aromatic ring optionally having substituent(s), or a salt thereof, and (2) a hydrophilic polymer (e.g., a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose) using a rotating blade fluidizing granulator, wherein the following conditions are set;
(i) adhesion to a nozzle of the rotating blade fluidizing granulator is prevented,
(ii) drying conditions: inlet air temperature is 55 to 75° C., preferably 60 to 70° C., and inlet air flow is 1.0 to 3.0 m$^3$/min, preferably 1.5 to 2.5 m$^3$/min, per 3.5 L of effective capacity of the rotating blade fluidizing granulator,
(iii) temperature conditions: product temperature is 25 to 35° C., preferably 25 to 30° C.,
(iv) humidity conditions: exhaustion humidity is 60 to 95% RH, preferably 60 to 90% RH, more preferably 70 to 80% RH, and
(v) spray rate: spray rate is 20 to 40 g/min, preferably 25 to 35 g/min, per 3.5 L of effective capacity of the rotating blade fluidizing granulator,
[38] a granule wherein a core particle is coated with (1) a physiologically active substance, which is a compound represented by the formula:

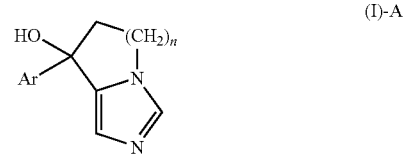

wherein n is an integer of 1 to 3, and Ar is an aromatic ring optionally having substituent(s), or a salt thereof and (2) a hydrophilic polymer (e.g., a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose), which is produced by the production method of the above-mentioned [37],

[39] a pharmaceutical composition comprising the granule of the above-mentioned [38],
[40] the pharmaceutical composition of the above-mentioned [39], which is an agent for the prophylaxis or treatment of prostate cancer, breast cancer, uterine cancer or ovarian cancer,
[41] a method for the prophylaxis or treatment of prostate cancer, breast cancer, uterine cancer or ovarian cancer, which comprises administering an effective amount of the pharmaceutical composition of the above-mentioned [39] to a mammal,
[42] use of the pharmaceutical composition of the above-mentioned [39] for the production of an agent for the prophylaxis or treatment of prostate cancer, breast cancer, uterine cancer or ovarian cancer,
[43] a method of producing a granule comprising coating a core particle with a physiologically active substance and a disintegrant using a rotating blade fluidizing granulator, wherein the following conditions are set;
(i) humidity conditions: exhaustion humidity is 60 to 95% RH, and
(ii) the disintegrant is croscarmellose sodium or microcrystalline cellulose,
[44] the production method of the above-mentioned [43], wherein the following conditions are set;
(i) adhesion to a nozzle of the rotating blade fluidizing granulator is prevented,
(ii) drying conditions: inlet air temperature is 55 to 75° C., and inlet air flow is 1.0 to 3.0 m³/min per 3.5 L of effective capacity of the rotating blade fluidizing granulator,
(iii) temperature conditions: product temperature is 25 to 35° C.,
(iv) humidity conditions: exhaustion humidity is 60 to 95% RH,
(v) spray rate: spray rate is 20 to 40 g/min per 3.5 L of effective capacity of the rotating blade fluidizing granulator, and
(vi) the disintegrant is croscarmellose sodium or microcrystalline cellulose,
[45] the production method of the above-mentioned [43] or [44], wherein the core particle is coated with a hydrophilic polymer and (or) an excipient besides the physiologically active substance and the disintegrant,
[46] a granule wherein a core particle is coated with a physiologically active substance and a disintegrant, which is produced by the production method of the above-mentioned [43],
[47] a pharmaceutical composition comprising the granule of the above-mentioned [46], and
[48] the pharmaceutical composition of the above-mentioned [47], which is a controlled release capsule preparation for oral administration, and the like.

BEST MODE FOR CARRYING OUT THE INVENTION

The "controlled release capsule preparation for oral administration" as used herein means a composition for which the release profile after oral administration of the physiologically active substance contained in the capsule preparation is controlled in a manner different from the release profile shown in administration of the physiologically active substance and includes any of those capsule preparation for which the release rate is controlled to be lower (sustained release), those compositions for which the release rate is controlled to be higher (accelerated dissolution), and those compositions for which the time for initiation of release is controlled (delayed dissolution), further including those compositions for which two or more of these controlling fashions are combined. The controlled release capsule preparation for oral administration of the invention (hereinafter, may be simply referred to as "controlled release capsule preparation") also includes those compositions for which release is not necessarily controlled over the entire process of dissolution, and release is controlled in a part of the process.

Preferred examples of the compound represented by the formula (I)-A include the following compounds:
[1] A compound wherein Ar is a monocyclic or bicyclic fused aromatic ring optionally having substituent(s);
[2] A compound wherein Ar is an aromatic ring optionally having substituent(s) and which consists of 5 to 10 atoms including 0 to 4 heteroatoms as a ring-constituting atom, bonded via carbon atoms;
[3] A compound wherein Ar is a group represented by the formula:

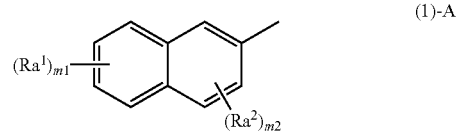

wherein m1 is an integer of 1 to 4, m2 is an integer of 0 to 3, and $Ra^1$ and $Ra^2$ are identical with or different from each other and are each a hydrogen atom, a hydroxyl group optionally having substituent(s), a thiol group optionally having substituent(s), an amino group optionally having substituent(s), an acyl group, a halogen atom, or a hydrocarbon group optionally having substituent(s),
a group represented by the formula:

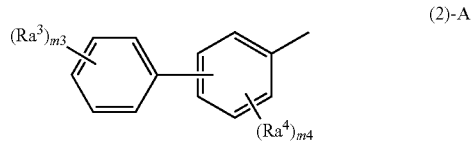

wherein m3 is an integer of 1 to 5, m4 is an integer of 0 to 4, and $Ra^3$ and $Ra^4$ are identical with or different from each other and are each a hydrogen atom, a hydroxyl group optionally having substituent(s), a thiol group optionally having substituent(s), an amino group optionally having substituent(s), an acyl group, a halogen atom, or a hydrocarbon group optionally having substituent(s), or
a group represented by the formula:

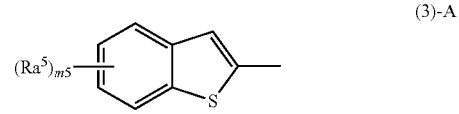

wherein m5 is an integer of 1 to 4, and $Ra^5$ is a hydrogen atom, a hydroxyl group optionally having substituent(s), a thiol group optionally having substituent(s), an amino group optionally having substituent(s), an acyl group, a halogen atom, or a hydrocarbon group optionally having substituent(s);

[4] A compound wherein Ar is a group represented by the formula:

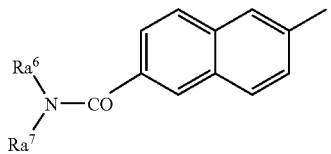
(1-1)-A wherein $Ra^6$ and $Ra^7$ are identical with or different from each other and are each a hydrogen atom or a lower alkyl group, or a group represented by the formula:

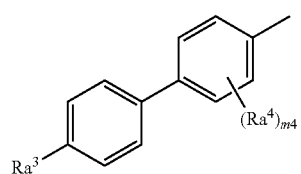
(2-1)-A wherein m4 is an integer of 0 to 4, and $Ra^3$ and $Ra^4$ are identical with or different from each other and are each a hydrogen atom, a hydroxyl group optionally having substituent(s), a thiol group optionally having substituent(s), an amino group optionally having substituent(s), an acyl group, a halogen atom, or a hydrocarbon group optionally having substituent(s);

[5] A compound wherein Ar is a group represented by the formula:

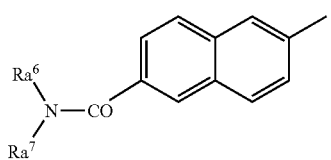
(1-1)-A wherein $Ra^6$ and $Ra^7$ are identical with or different from each other and are each a hydrogen atom or a lower alkyl group;
[6] A compound which is an enantiomer whose configuration is (S); and
[7] A compound which is an enantiomer whose configuration is (R) and the like can be mentioned.

Each symbol in each the formula is defined as follows.
n is an integer of 1 to 3, with preference given to 1.
m1 is an integer of 1 to 4, with preference given to 1 or 2, particularly 1.
m2 is an integer of 0 to 3, with preference given to 0 or 1, particularly 0.
m3 is an integer of 1 to 5, with preference given to 1 to 3, particularly 1.
m4 is an integer of 0 to 4, with preference given to 0 or 1, particularly 0.
m5 is an integer of 1 to 4, with preference given to 1 or 2, particularly 1.

The hydroxyl group optionally having substituent(s) represented by $Ra^1$, $Ra^2$, $Ra^3$, $Ra^4$ and $Ra^5$ may be exemplified by, in addition to an unsubstituted hydroxyl group, a lower alkoxy (e.g., $C_{1-4}$ alkoxy such as methoxy, ethoxy and propoxy), a lower alkanoyloxy (e.g., $C_{1-4}$ alkanoyloxy such as acetyloxy and propionyloxy), a carbamoyloxy optionally having substituent(s) (in addition to an unsubstituted carbamoyloxy, a carbamoyloxy substituted with one or two $C_{1-4}$ alkyls, such as, for example, methylcarbamoyloxy, ethylcarbamoyloxy, dimethylcarbamoyloxy, diethylcarbamoyloxy and ethylmethylcarbamoyloxy), and the like.

The thiol optionally having substituent(s) represented by $Ra^1$, $Ra^2$, $Ra^3$, $Ra^4$ and $Ra^5$ may be exemplified by, in addition to an unsubstituted thiol, a lower alkylthio (e.g., $C_{1-4}$ alkylthio such as methylthio, ethylthio and propylthio), a lower alkanoylthio group (e.g., $C_{1-4}$ alkanoylthio such as acetylthio and propionylthio), and the like.

The amino optionally having substituent(s) represented by $Ra^1$, $Ra^2$, $Ra^3$, $Ra^4$ and $Ra^5$ may be exemplified by, in addition to an unsubstituted amino, a lower alkylamino (e.g., $C_{1-4}$ alkylamino such as methylamino, ethylamino and propylamino), a di-lower alkylamino (e.g., di-$C_{1-4}$ alkylamino such as dimethylamino and diethylamino), $C_{1-4}$ alkanoylamino (e.g., acetylamino, propionylamino, etc.), and the like.

The acyl represented by $Ra^1$, $Ra^2$, $Ra^3$, $Ra^4$ and $Ra^5$ may be exemplified by alkanoyl (e.g., $C_{1-6}$ alkanoyl such as formyl, acetyl and propionyl), alkylsulfonyl (e.g., $C_{1-4}$ alkylsulfonyl such as methylsulfonyl and ethylsulfonyl), aroyl (e.g., benzoyl, toluoyl, naphthoyl, etc.), a carbamoyl optionally having substituent(s) (e.g., mono- or di-$C_{1-10}$ alkylcarbamoyl such as methylcarbamoyl, ethylcarbamoyl, dimethylcarbamoyl and diethylcarbamoyl; mono- or di-$C_{6-14}$ arylcarbamoyl such as, for example, phenylcarbamoyl and diphenylcarbamoyl; mono- or di-$C_{7-16}$ aralkylcarbamoyl such as, for example, benzylcarbamoyl and dibenzylcarbamoyl; etc.), a sulfamoyl optionally having substituent(s) (e.g., mono- or di-$C_{1-10}$ alkylsulfamoyl such as methylsulfamoyl, ethylsulfamoyl, dimethylsulfamoyl and diethylsulfamoyl; mono- or di-$C_{6-14}$ arylsulfamoyl such as, for example, phenylsulfamoyl and diphenylsulfamoyl; mono- or di-$C_{7-16}$ aralkylsulfamoyl such as, for example, benzylsulfamoyl and dibenzylsulfamoyl; etc.), and the like.

As the halogen for $Ra^1$, $Ra^2$, $Ra^3$, $Ra^4$ or $Ra^5$, fluorine, chlorine, bromine and iodine can be mentioned.

The "hydrocarbon group" of the "hydrocarbon group optionally having substituent(s)" represented by $Ra^1$, $Ra^2$, $Ra^3$, $Ra^4$ and $Ra^5$ may be exemplified by a chain hydrocarbon group, a cyclic hydrocarbon group or the like.

The chain hydrocarbon group may be exemplified by a straight-chained or branched hydrocarbon group having 1 to 10 carbon atoms or the like, and specifically by alkyl, alkenyl, alkynyl or the like. Among these, alkyl is particularly preferred. Examples of the "alkyl" include $C_{1-10}$ alkyl such as methyl, ethyl, propyl, isopropyl, butyl, isobutyl, sec-butyl, tert-butyl, pentyl, isopentyl, neopentyl, hexyl and isohexyl, and the like, and preferred is $C_{1-6}$ alkyl (e.g., methyl, ethyl, propyl, isopropyl, butyl, sec-butyl, tert-butyl, etc.). Examples of the "alkenyl" include $C_{2-10}$ alkenyl such as vinyl, 1-propenyl, allyl, isopropenyl, 1-butenyl, 2-butenyl, 3-butenyl, isobutenyl and sec-butenyl, and the like, and preferred is $C_{2-6}$ alkenyl (e.g., vinyl, 1-propenyl, allyl, etc.). Examples of the "alkynyl" include $C_{2-10}$ alkynyl such as ethynyl, 1-propynyl and propargyl, and the like, and preferred is $C_{2-6}$ alkynyl (e.g., ethynyl, etc.).

The cyclic hydrocarbon group may be exemplified by a cyclic hydrocarbon group having 3 to 18 carbon atoms, and specifically by an alicyclic hydrocarbon group, an aromatic hydrocarbon group or the like.

The "alicyclic hydrocarbon group" may be exemplified by a monocyclic or fused polycyclic group having 3 to 10 carbon atoms, and specifically by cycloalkyl, cycloalkenyl and bi- or tricyclic fused rings formed therefrom with $C_{6-14}$ aryl (e.g., benzene, etc.), or the like. Examples of the "cycloalkyl" include $C_{3-6}$ cycloalkyl such as cyclopropyl, cyclobutyl, cyclopentyl and cyclohexyl, and the like, and examples of the "cycloalkenyl" include $C_{3-6}$ cycloalkenyl such as cyclopropenyl, cyclobutenyl, cyclopentenyl and cyclohexenyl, and the like.

The "aromatic hydrocarbon group" may be exemplified by a monocyclic aromatic hydrocarbon group or a fused polycyclic aromatic hydrocarbon group consisting of 6 to 18 carbon atoms, or the like, and specifically by $C_{6-14}$ aryl such as phenyl, 1-naphthyl, 2-naphthyl, 2-indenyl and 2-anthryl, and the like. $C_{6-10}$ aryl (e.g., phenyl, etc.) or the like is preferred.

The substituent which may be carried by the "chain hydrocarbon group" of the "hydrocarbon group optionally having substituent(s)" is not particularly limited, and examples thereof include a halogen atom, a hydroxyl group, alkoxy, acyloxy, alkylthio, acylamino, carboxyl, alkoxycarbonyl, oxo, alkylcarbonyl, cycloalkyl, aryl, an aromatic heterocyclic group and the like. These substituents are substituted on the "chain hydrocarbon group" to a chemically acceptable extent, and the number of the substituents is from 1 to 5, and preferably from 1 to 3, provided that when the number of the substituents is two or more, they may be identical with or different from each other.

The substituent which may be carried by the "cyclic hydrocarbon group" of the "hydrocarbon group optionally having substituent(s)" is not particularly limited, and examples thereof include a halogen atom, a hydroxyl group, alkoxy, acyloxy, alkylthio, alkylsulfonyl, mono- or dialkylamino, acylamino, carboxyl, alkoxycarbonyl, alkynylcarbonyl, alkyl, cycloalkyl, aryl, an aromatic heterocyclic group and the like. These substituents are substituted on the "cyclic hydrocarbon group" to a chemically acceptable extent, and the number of the substituents is from 1 to 5, and preferably from 1 to 3, provided that when the number of the substituents is two or more, they may be identical with or different from each other.

Examples of the "halogen atom" include fluorine, chlorine, bromine and iodine. Examples of the "alkoxy" include $C_{1-10}$ alkoxy such as methoxy, ethoxy, propoxy, isopropoxy, butoxy, isobutoxy, sec-butoxy, pentyloxy and hexyloxy, and the like. Examples of the "acyloxy" include formyloxy, $C_{1-10}$ alkyl-carbonyloxy (e.g., acetoxy, propionyloxy, etc.) and the like. Examples of the "alkylthio" include $C_{1-10}$ alkylthio such as methylthio, ethylthio, propylthio and isopropylthio, and the like. Examples of the "alkylsulfonyl" include $C_{1-10}$ alkylsulfonyl such as methylsulfonyl, ethylsulfonyl and propylsulfonyl, and the like. Examples of the "acylamino" include formylamino, diformylamino, mono- or di-$C_{1-10}$ alkyl-carbonylamino (e.g., acetylamino, propionylamino, butyrylamino, diacetylamino, etc.) and the like. The "mono- or dialkylamino" is exemplified by the same lower alkylamino or di-lower alkylamino described above. Examples of the "alkoxycarbonyl" include $C_{1-10}$ alkoxycarbonyl such as methoxycarbonyl, ethoxycarbonyl, propoxycarbonyl, isopropoxycarbonyl and butoxycarbonyl, and the like. Examples of the "alkylcarbonyl" include $C_{1-10}$ alkylcarbonyl such as acetyl, propionyl, butyryl and valeryl, and the like. Examples of the "alkynylcarbonyl" include $C_{3-10}$ alkynylcarbonyl such as ethynylcarbonyl, 1-propynylcarbonyl and 2-propynylcarbonyl, and the like. Examples of the "cycloalkyl" include $C_{3-10}$ cycloalkyl such as cyclopropyl, cyclobutyl, cyclopentyl and cyclohexyl, and the like. Examples of the "aryl" include $C_{6-14}$ aryl such as phenyl, 1-naphthyl and 2-naphthyl, and the like. The "aromatic heterocyclic group" may be exemplified by monocyclic to tricyclic aromatic heterocyclic groups containing, in addition to carbon atoms, preferably 1 to 4 heteroatoms of one or two kinds selected from nitrogen, oxygen and sulfur, or the like. Specific examples thereof include thienyl, pyridyl, furyl, pyrazinyl, pyrimidinyl, imidazolyl, pyrazolyl, thiazolyl, isothiazolyl, oxazolyl, isoxazolyl, pyridazinyl, tetrazolyl, quinolyl, indolyl, isoindolyl and the like. Examples of the "alkyl" include $C_{1-10}$ alkyl such as methyl, ethyl, propyl, isopropyl, butyl, sec-butyl, tert-butyl and pentyl, and the like.

The substituent which may be carried by the above-mentioned "hydrocarbon group" may further have, to a chemically acceptable extent, 1 to 5, and preferably 1 to 3 substituents which are described below. Examples of such substituent include a halogen atom (e.g., fluorine, chlorine and bromine), a hydroxyl group, and $C_{1-6}$ alkoxy (e.g., methoxy, ethoxy, propoxy, isopropoxy, etc.).

The lower alkyl group represented by $Ra^6$ and $Ra^7$ is exemplified by a straight-chained, branched or cyclic alkyl group having 1 to 4 carbon atoms, and examples thereof include methyl, ethyl, propyl, isopropyl, butyl, isobutyl, sec-butyl, tert-butyl, cyclopropyl, cyclobutyl and the like.

The aromatic ring optionally having substituent(s) represented by Ar is exemplified by a monocyclic or bicyclic aromatic fused ring which may have 1 or more substituents, or the like. Further, an aromatic ring optionally having substituent(s) and consisting of 5 to 10 atoms including 0 to 4 heteroatoms as the ring-constituting atom (here, the aromatic ring is bonded to the fused imidazole ring of the formula (I)-A via carbon atoms, not via heteroatoms) is also a suitable example of Ar.

The substituent of the aromatic ring optionally having substituent(s) represented by Ar may be exemplified by a hydroxyl group optionally having substituent(s), a thiol optionally having substituent(s), an amino optionally having substituent(s), an acyl group, a halogen atom, or a hydrocarbon group optionally having substituent(s). The "hydroxyl group optionally having substituent(s)", the "amino optionally having substituent(s)", the "acyl", the "halogen atom" and the "hydrocarbon group optionally having substituent(s)" may be exemplified by those exemplified in the above as $Ra^1$, $Ra^2$, $Ra^3$, $Ra^4$ and $Ra^5$, respectively.

The compound represented by the formula (I)-A may be in the form of a salt, and examples of the salt include acid addition salts, for example, inorganic acid salts (e.g., hydrochloride, sulfate, hydrobromide, phosphate, etc.), organic acid salts (e.g., acetate, trifluoroacetate, succinate, maleate, fumarate, propionate, citrate, tartrate, lactate, oxalate, methanesulfonate, p-toluenesulfonate, etc.) and the like.

Furthermore, the compound represented by the formula (I)-A or a salt thereof may be in the form of a hydrate, and any of these fall within the scope of the invention. Hereinafter, salts and hydrates are also included into what is referred to as compound (I)-A.

The compound represented by the formula (I)-A and a prodrug thereof have excellent effect as a medicine and particularly have excellent inhibitory activity against steroid $C_{17,20}$-lyase. These compounds have low toxicity and few side effects.

Therefore, the controlled release capsule preparation of the present invention containing a compound represented by the formula (I)-A and a prodrug thereof is useful, for mammals (e.g., a human, a cow, a horse, a pig, a dog, a cat, a monkey, a mouse, a rat, etc., especially a human), for example, as (i) an androgen or estrogen-lowering drug [i.e., a medicine having an inhibitory action on production of androgen and subsequent production of estrogen (estrogen is synthesized from androgen as the substrate)], and (ii) a therapeutic and prophylactic drug for the diseases related to androgen or estrogen, for example, (1) primary cancer, metastasis or recurrence of malignant tumors (e.g., prostate cancer, breast cancer, uterine cancer, ovarian cancer, etc.), (2) symptoms associated with those cancers (e.g., pain, cachexia, etc.), and (3) various diseases such as benign prostatic hypertrophy, virilism, hypertrichosis, male pattern baldness, sexual precocity in boys, endometriosis, hysteromyoma, uterine adenomyosis, mastopathy and polycystic ovarian syndrome, and preferably prostate cancer, breast cancer and the like.

Moreover, the controlled release capsule preparation of the present invention is also useful as an agent for the prophylaxis or treatment of androgen-independent prostate cancer (AIPC), hormone-naive prostate cancer (HNPC) and the like.

The prodrug of compound (I)-A refers to a compound which is converted to compound (I)-A by an in vivo reaction under the action of enzyme, gastric acid or the like. Since the prodrug exhibits steroid $C_{17,20}$-lyase inhibitory activity upon conversion to compound (I)-A in vivo, it is to be included in the physiologically active substance contained in the controlled release capsule preparation of the invention.

Examples of the prodrug of compound (I)-A include compounds resulting from acylation or alkylation of the imidazole nitrogen of compound (I)-A (e.g., compound which is subjected to dimethylaminosulfonylation, acetoxymethylation, (5-methyl-2-oxo-1,3-dioxolen-4-yl)methoxycarbonylmethylation, pivaloyloxymethylation, benzyloxymethylation, etc.); compounds resulting from acylation, alkylation, phosphorylation, sulfation or boration of the hydroxyl group of compound (I)-A (e.g., compound in which the hydroxyl group of compound (I)-A is in the form of acetyl, palmitoyl, propanoyl, pivaloyl, succinyl, fumaryl, alanyl, dimethylaminomethylcarbonyl or the like); and the like. These compounds can be prepared by those methods known per se in the art.

The prodrug of compound (I)-A may exist as such or as a pharmaceutically acceptable salt. Examples of such salt include, in the case where the prodrug of compound (I)-A has an acidic group such as carboxyl, salts formed with inorganic bases (e.g., alkali metals such as sodium and potassium; alkaline earth metals such as calcium and magnesium; transition metals such as zinc, iron and copper; etc.), organic bases (e.g., organic amines such as trimethylamine, triethylamine, pyridine, picoline, ethanolamine, diethanolamine, triethanolamine, dicyclohexylamine, N,N'-dibenzylethylenediamine, tromethamine[tris(hydroxymethyl)methylamine] and tert-butylamine; basic amino acids such as arginine, lysine or ornithine; etc.), and the like.

In the case where the prodrug of compound (I)-A has a basic group such as amino, examples of the salt include salts formed with inorganic acids or organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.), acidic amino acids such as aspartic acid and glutamic acid, and the like.

The prodrug of the compound (I)-A may be a hydrate or a non-hydrate.

While the compound (I)-A has one or more asymmetric carbons in a molecule, both an R configuration compound and an S configuration compound due to the asymmetric carbons are encompassed in the present invention.

As the compound (I)-A, a compound, wherein the absolute configuration of carbon atom bonded by hydroxy group is S configuration, is preferable.

Of the compounds represented by the formula (I)-A,
(±)-7-(5-methoxybenzo[b]thiophen-2-yl)-6,7-dihydro-5H-pyrrolo[1,2-c]imidazol-7-ol,
(±)-7-(5-fluorobenzo[b]thiophen-2-yl)-6,7-dihydro-5H-pyrrolo[1,2-c]imidazol-7-ol,
(±)-7-(4'-fluoro[1,1'-biphenyl]-3-yl)-6,7-dihydro-5H-pyrrolo[1,2-c]imidazol-7-ol,
(±)-7-(4'-fluoro[1,1'-biphenyl]-4-yl)-6,7-dihydro-5H-pyrrolo[1,2-c]imidazol-7-ol,
(±)-6-(7-hydroxy-6,7-dihydro-5H-pyrrolo[1,2-c]imidazol-7-yl)-N-methyl-2-naphthamide,
(±)-N-cyclopropyl-6-(7-hydroxy-6,7-dihydro-5H-pyrrolo[1,2-c]imidazol-7-yl)-2-naphthamide,
(±)-N-ethyl-6-(7-hydroxy-6,7-dihydro-5H-pyrrolo[1,2-c]imidazol-7-yl)-2-naphthamide,
(±)-N-cyclobutyl-6-(7-hydroxy-6,7-dihydro-5H-pyrrolo[1,2-c]imidazol-7-yl)-2-naphthamide,
(±)-6-(7-hydroxy-6,7-dihydro-5H-pyrrolo[1,2-c]imidazol-7-yl)-N-isopropyl-2-naphthamide,
(±)-6-(7-hydroxy-6,7-dihydro-5H-pyrrolo[1,2-c]imidazol-7-yl)-2-naphthamide,
(+)-7-(5-methoxybenzo[b]thiophen-2-yl)-6,7-dihydro-5H-pyrrolo[1,2-c]imidazol-7-ol,
(+)-7-(5-fluorobenzo[b]thiophen-2-yl)-6,7-dihydro-5H-pyrrolo[1,2-c]imidazol-7-ol,
(+)-7-(4'-fluoro[1,1'-biphenyl]-3-yl)-6,7-dihydro-5H-pyrrolo[1,2-c]imidazol-7-ol,
(+)-7-(4'-fluoro[1,1'-biphenyl]-4-yl)-6,7-dihydro-5H-pyrrolo[1,2-c]imidazol-7-ol,
(+)-6-(7-hydroxy-6,7-dihydro-5H-pyrrolo[1,2-c]imidazol-7-yl)-N-methyl-2-naphthamide,
(+)-N-cyclopropyl-6-(7-hydroxy-6,7-dihydro-5H-pyrrolo[1,2-c]imidazol-7-yl)-2-naphthamide,
(+)-N-ethyl-6-(7-hydroxy-6,7-dihydro-5H-pyrrolo[1,2-c]imidazol-7-yl)-2-naphthamide,
(+)-N-cyclobutyl-6-(7-hydroxy-6,7-dihydro-5H-pyrrolo[1,2-c]imidazol-7-yl)-2-naphthamide,
(+)-6-(7-hydroxy-6,7-dihydro-5H-pyrrolo[1,2-c]imidazol-7-yl)-N-isopropyl-2-naphthamide,
(+)-6-(7-hydroxy-6,7-dihydro-5H-pyrrolo[1,2-c]imidazol-7-yl)-2-naphthamide,
(−)-7-(5-methoxybenzo[b]thiophen-2-yl)-6,7-dihydro-5H-pyrrolo[1,2-c]imidazol-7-ol,
(−)-7-(5-fluorobenzo[b]thiophen-2-yl)-6,7-dihydro-5H-pyrrolo[1,2-c]imidazol-7-ol,
(−)-7-(4'-fluoro[1,1'-biphenyl]-3-yl)-6,7-dihydro-5H-pyrrolo[1,2-c]imidazol-7-ol,
(−)-7-(4'-fluoro[1,1'-biphenyl]-4-yl)-6,7-dihydro-5H-pyrrolo[1,2-c]imidazol-7-ol,
(−)-6-(7-hydroxy-6,7-dihydro-5H-pyrrolo[1,2-c]imidazol-7-yl)-N-methyl-2-naphthamide,
(−)-N-cyclopropyl-6-(7-hydroxy-6,7-dihydro-5H-pyrrolo[1,2-c]imidazol-7-yl)-2-naphthamide,
(−)-N-ethyl-6-(7-hydroxy-6,7-dihydro-5H-pyrrolo[1,2-c]imidazol-7-yl)-2-naphthamide,
(−)-N-cyclobutyl-6-(7-hydroxy-6,7-dihydro-5H-pyrrolo[1,2-c]imidazol-7-yl)-2-naphthamide,
(−)-6-(7-hydroxy-6,7-dihydro-5H-pyrrolo[1,2-c]imidazol-7-yl)-N-isopropyl-2-naphthamide,
(−)-6-(7-hydroxy-6,7-dihydro-5H-pyrrolo[1,2-c]imidazol-7-yl)-2-naphthamide,
(+)-6-(7-hydroxy-6,7-dihydro-5H-pyrrolo[1,2-c]imidazol-7-yl)-2-naphthamide,
(−)-6-(7-hydroxy-6,7-dihydro-5H-pyrrolo[1,2-c]imidazol-7-yl)-2-naphthamide and the like are preferable. Particularly, (+)-6-(7-hydroxy-6,7-dihydro-5H-pyrrolo[1,2-c]imidazol-7-yl)-N-methyl-2-naphthamide is preferable.

The compound represented by the formula (I)-A can be prepared by, for example, the method disclosed in WO 02/40484.

Preferably, the physiologically active substance contained in the controlled release capsule preparation of the invention exhibits high water solubility under acidic conditions, and specifically, the solubility of the substance at 37° C. with respect to $1^{st}$ fluid for the disintegration test in the Japanese Pharmacopoeia (hereinafter, may be abbreviated as "solubility (Pharmacopoeia $1^{st}$ fluid, 37° C.)") is about 0.1 mg/mL or more, preferably about 1 mg/mL or more, and more preferably about 5 mg/mL or more.

The "hydrophilic polymers" contained in the controlled release capsule preparation of the invention refers to polymers which become hydrogel upon absorption of water, and then allow diffusion of the physiologically active substance dispersed in the gel, or become able to control release of the physiologically active substance by dissolution of the polymer itself in water, or control release of the physiologically active substance not by dissolution but by swelling in water.

The viscosity of the hydrophilic polymer is, for example, as the viscosity of a 2 wt % aqueous solution (measurement temperature: 20° C.), preferably 1 mPa·s or more, and more preferably 4 mPa·s or more. With respect to the controlled release capsule preparation of the invention, it is possible to arbitrarily control the duration of release of the physiologically active substance from the composition by adjusting the viscosity of the hydrophilic polymer which is used as the base capable of controlled release, or mixing ratio thereof, or the like.

Specific examples of the hydrophilic polymer include:

hydroxypropylcellulose such as HPC-SSL (tradename, Nippon Soda Co., Ltd.) (viscosity of 2 wt % aqueous solution at 20° C.: 2.0 to 2.9 mPa·s), HPC-SL (tradename, Nippon Soda Co., Ltd.) (viscosity of 2 wt % aqueous solution at 20° C.: 3.0 to 5.9 mPa·s), HPC-SL-T (tradename, Nippon Soda Co., Ltd.) (viscosity of 2 wt % aqueous solution at 20° C.: 1.2 to 3.7 mPa·s), HPC-L (tradename, Nippon Soda Co., Ltd.) (viscosity of 2 wt % aqueous solution at 20° C.: 6.0 to 10.0 mPa·s), HPC-M (tradename, Nippon Soda Co., Ltd.) (viscosity of 2 wt % aqueous solution at 20° C.: 150 to 400 mPa·s), HPC-H (tradename, Nippon Soda Co., Ltd.) (viscosity of 2 wt % aqueous solution at 20° C.: 1000 to 4000 mPa·s), and the like, particularly HPC-SL-T (tradename, Nippon Soda Co., Ltd.);

hydroxypropylmethylcellulose such as TC-5E (tradename, Shin-Etsu Chemical Co., Ltd.) (viscosity of 2 wt % aqueous solution at 20° C.: about 3 mPa·s), TC-5EW (tradename, Shin-Etsu Chemical Co., Ltd.) (viscosity of 2 wt % aqueous solution at 20° C.: about 3 mPa·s), SB-4 (tradename, Shin-Etsu Chemical Co., Ltd.) (viscosity of 2 wt % aqueous solution at 20° C.: about 4 mPa·s), TC-5MW (tradename, Shin-Etsu Chemical Co., Ltd.) (viscosity of 2 wt % aqueous solution at 20° C.: about 4.5 mPa·s), TC-5R (tradename, Shin-Etsu Chemical Co., Ltd.) (viscosity of 2 wt % aqueous solution at 20° C.: about 6 mPa·s), TC-5RW (tradename, Shin-Etsu Chemical Co., Ltd.) (viscosity of 2 wt % aqueous solution at 20° C.: about 6 mPa·s), TC-5S (tradename, Shin-Etsu Chemical Co., Ltd.) (viscosity of 2 wt % aqueous solution at 20° C.: about 15 mPa·s), Metolose 60SH-50 (tradename, Shin-Etsu Chemical Co., Ltd.) (viscosity of 2 wt % aqueous solution at 20° C.: about 50 mPa·s), Metolose 65SH-50 (tradename, Shin-Etsu Chemical Co., Ltd.) (viscosity of 2 wt % aqueous solution at 20° C.: about 50 mPa·s), Metolose 90SH-100 (tradename, Shin-Etsu Chemical Co., Ltd.) (viscosity of 2 wt % aqueous solution at 20° C.: about 100 mPa·s), Metolose 65SH-400 (tradename, Shin-Etsu Chemical Co., Ltd.) (viscosity of 2 wt % aqueous solution at 20° C.: about 400 mPa·s), Metolose 90SH-400 (tradename, Shin-Etsu Chemical Co., Ltd.) (viscosity of 2 wt % aqueous solution at 20° C.: about 400 mPa·s), Metolose 65SH-1500 (tradename, Shin-Etsu Chemical Co., Ltd.) (viscosity of 2 wt % aqueous solution at 20° C.: about 1500 mPa·s), Metolose 60SH-4000 (tradename, Shin-Etsu Chemical Co., Ltd.) (viscosity of 2 wt % aqueous solution at 20° C.: about 4000 mPa·s), Metolose 65SH-4000 (tradename, Shin-Etsu Chemical Co., Ltd.) (viscosity of 2 wt % aqueous solution at 20° C.: about 4000 mPa·s), Metolose 90SH-4000 (tradename, Shin-Etsu Chemical Co., Ltd.) (viscosity of 2 wt % aqueous solution at 20° C.: about 4000 mPa·s), Metolose 90SH-30000 (tradename, Shin-Etsu Chemical Co., Ltd.) (viscosity of 2 wt % aqueous solution at 20° C.: about 30000 mPa·s), and the like, particularly TC-5EW (tradename, Shin-Etsu Chemical Co., Ltd.);

methylcellulose such as Metolose SM15 (tradename, Shin-Etsu Chemical Co., Ltd.) (viscosity of 2 wt % aqueous solution at 20° C.: about 15 mPa·s), Metolose SM25 (tradename, Shin-Etsu Chemical Co., Ltd.) (viscosity of 2 wt % aqueous solution at 20° C.: about 25 mPa·s), Metolose SM100 (tradename, Shin-Etsu Chemical Co., Ltd.) (viscosity of 2 wt % aqueous solution at 20° C.: about 100 mPa·s), Metolose SM400 (tradename, Shin-Etsu Chemical Co., Ltd.) (viscosity of 2 wt % aqueous solution at 20° C.: about 400 mPa·s), Metolose SM1500 (tradename, Shin-Etsu Chemical Co., Ltd.) (viscosity of 2 wt % aqueous solution at 20° C.: about 1500 mPa·s), Metolose SM4000 (tradename, Shin-Etsu Chemical Co., Ltd.) (viscosity of 2 wt % aqueous solution at 20° C.: about 4000 mPa·s), Metolose SM8000 (tradename, Shin-Etsu Chemical Co., Ltd.) (viscosity of 2 wt % aqueous solution at 20° C.: about 8000 mPa·s), and the like;

polyethylene oxide such as WSR N-12K (tradename, Union Carbide Corp.) (viscosity of 2 wt % aqueous solution at 20° C.: 400 to 800 mPa·s), WSR N-60K (tradename, Union Carbide Corp.) (viscosity of 2 wt % aqueous solution at 20° C.: 2000 to 4000 mPa·s), WSR 301 (tradename, Union Carbide Corp.) (viscosity of 1 wt % aqueous solution at 25° C.: 1500 to 4500 mPa·s), WSR Coagulant (tradename, Union Carbide Corp.) (viscosity of 1 wt % aqueous solution at 25° C.: 4500 to 7500 mPa·s), WSR 303 (tradename, Union Carbide Corp.) (viscosity of 1 wt % aqueous solution at 25° C.: 7500 to 10000 mPa·s), WSR 308 (tradename, Union Carbide Corp.) (viscosity of 1 wt % aqueous solution at 25° C.: 10000 to 15000 mPa·s), and the like;

sodium carboxymethylcellulose such as Sanlose F-150MC (tradename, Nippon Paper Group, Inc.) (viscosity of 1 wt % aqueous solution at 25° C.: 1200 to 1800 mPa·s), Sanlose F-300MC (tradename, Nippon Paper Group, Inc.) (viscosity of 1 wt % aqueous solution at 25° C.: 2500 to 3000 mPa·s), Sanlose F-1000MC (tradename, Nippon Paper Group, Inc.) (viscosity of 1 wt % aqueous solution at 25° C.: 8000 to 12000 mPa·s), and the like;

low-substituted hydroxypropylcellulose such as LH-11 (tradename, Shin-Etsu Chemical Co., Ltd.), LH-21 (tradename, Shin-Etsu Chemical Co., Ltd.), LH-31 (tradename, Shin-Etsu Chemical Co., Ltd.), LH-22 (tradename, Shin-Etsu Chemical Co., Ltd.), LH-32 (tradename, Shin-Etsu Chemical Co., Ltd.), LH-20 (tradename, Shin-Etsu Chemical Co., Ltd.), LH-30 (tradename, Shin-Etsu Chemical Co., Ltd.), and the like; and the like. These hydrophilic polymers may be used in a mixture of two or more kinds thereof at an appropriate ratio.

The content of the physiologically active substance in the controlled release capsule preparation of the invention varies depending on the kind of the physiologically active substance, the size of the preparation or the like, but it is, for example, about 1 to about 90% by weight, preferably about 5 to about 85% by weight, more preferably about 10 to about 80% by weight, and particularly preferably about 20 to about 40% by weight.

Further, the content of the hydrophilic polymer in the controlled release capsule preparation of the invention varies depending on the content of the physiologically active substance, the size of the preparation, the kind of the hydrophilic polymer or the like, but it is, for example, about 3 to about 90% by weight, preferably about 3 to about 90% by weight, more preferably about 3 to about 50% by weight and particularly preferably about 3 to about 10% by weight.

Since the above-described controlled release capsule preparation contains a granule containing the above-described physiologically active substance and the hydrophilic polymer at the above-described respective contents, immediate dissolution of the physiologically active substance at acidic pH (e.g., pH 1 to 3), which corresponds to the dissolution in the vicinity of stomach during the early stage of oral administration, is controlled; and dissolution of the physiologically active substance at weakly acidic to weakly alkaline pH (e.g., pH 5 to 8), which corresponds to the subsequent dissolution in the small intestine or thereafter, particularly in the duodenum to ileum, is sustained for a long time.

The above-mentioned granule containing the physiologically active substance and the hydrophilic polymer can be produced by mixing these components respectively at the above-mentioned contents and molding the mixture. Here, mixing and molding can be carried out according to methods that are conventionally used in the art of the formulation technology. The mode of dispersion of the physiologically active substance in the molded product may be homogeneous dispersion or heterogeneous dispersion, but homogeneous dispersion is preferred.

Furthermore, during the process of mixing and/or molding, a pharmaceutically acceptable carrier may be also used. Here, the "pharmaceutically acceptable carrier" refers to various organic or inorganic carrier materials that are conventionally used as a material for preparation, for example, an excipient, a lubricant, a binder, a disintegrant and the like. Particularly, an excipient and/or a disintegrant are/is preferably used. Further, if necessary, additives for preparation such as an antiseptic, an antioxidant, a colorant, a sweetener and the like can be also used.

As preferable examples of the excipient, lactose, sucrose, D-mannitol, D-sorbitol, starch, pregelatinized starch, dextrin, microcrystalline cellulose, low-substituted hydroxypropylcellulose, sodium carboxymethylcellulose, gum arabic, dextrin, pullulan, synthetic aluminum silicate, magnesium aluminometasilicate and the like can be mentioned. Of these, D-mannitol, microcrystalline cellulose and the like are preferable.

As preferable examples of the lubricant, magnesium stearate, calcium stearate, talc, colloid silica, synthetic aluminum silicate, magnesium aluminometasilicate and the like can be mentioned.

Preferred examples of the binder include pregelatinized starch, sugar, gelatin, gum arabic, methylcellulose, carboxymethylcellulose, sodium carboxymethylcellulose, microcrystalline cellulose, sucrose, D-mannitol, trehalose, dextrin, pullulan, hydroxypropylcellulose, hydroxypropylmethylcellulose, polyvinylpyrrolidone and the like.

As preferable examples of the disintegrant, lactose, sucrose, starch, carboxymethylcellulose, calcium carboxymethylcellulose, croscarmellose sodium, microcrystalline cellulose, sodium carboxymethylstarch, low-substituted hydroxypropylcellulose and the like can be mentioned. Of these, croscarmellose sodium, microcrystalline cellulose, low-substituted hydroxypropylcellulose and the like are preferable, and particularly croscarmellose sodium and microcrystalline cellulose are preferable.

Preferred examples of the antiseptic include paraoxybenzoic acid esters, chlorobutanol, benzyl alcohol, phenethyl alcohol, dehydroacetic acid, sorbic acid and the like.

Preferred examples of the antioxidant include sulfites, ascorbates and the like.

Preferred examples of the colorant include aqueous edible tar dyes (e.g., edible dyes such as Edible Red No. 2 and No. 3, Edible Yellow No. 4 and No. 5, Edible Blue No. 1 and No. 2, etc.), water-insoluble lake dyes (e.g., aluminum salts of the above-mentioned aqueous edible tar dyes), natural dyes (e.g., β-carotene, chlorophyll, Bengala) and the like.

Preferred examples of the sweetener include saccharin sodium, dipotassium glycyrrhizinate, aspartame, stevia and the like.

While the content of the carrier in the controlled release capsule preparation of the present invention varies depending on the kind of the physiologically active substance, kind of the carrier, size of the preparation and the like, it is, for example, about 1-about 94 wt %, about 1-about 90 wt %, preferably about 1-about 85 wt %, more preferably about 1-about 80 wt %, more preferably about 1-about 50 wt %, particularly preferably about 1-about 20 wt %, and most preferably about 1-about 10 wt %.

Particularly, while the content of the excipient and/or the disintegrant in the controlled release capsule preparation of the present invention varies depending on the content of the physiologically active substance, kind of the excipient and/or the disintegrant, size of the preparation and the like, it is, for example, about 1-about 50 wt %, preferably about 1-about 20 wt %, more preferably about 1-about 10 wt %.

Specifically, a preferable granule mentioned above contains (1) a physiologically active substance, which is a compound represented by the formula:

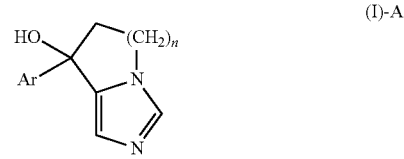

(I)-A wherein n is an integer of 1 to 3, and Ar is an aromatic ring optionally having substituent(s), or a salt thereof, (2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose, (3) an excipient selected from the group consisting of lactose, sucrose, D-mannitol, D-sorbitol, starch, pregelatinized starch, dextrin, microcrystalline cellulose, low-substituted hydroxypropylcellulose, sodium carboxymethylcellulose, gum arabic, dextrin, pullulan, synthetic aluminum silicate and magnesium aluminometasilicate (preferably, D-mannitol, microcrystalline cellulose) and (4) a disintegrant selected from the group consisting of lactose, sucrose, starch, carboxymethylcellulose, calcium carboxymethylcellulose, croscarmellose sodium, microcrystalline cellulose, sodium carboxymethyl starch and low-substituted hydroxypropylcellulose (preferably, croscarmellose sodium, microcrystalline cellulose, low-substituted hydroxypropylcellulose and the like, particularly preferably croscarmellose sodium, microcrystalline cellulose).

When the physiologically active substance contained in the above-described controlled release capsule preparation is, from weakly acidic to weakly alkaline, having relative low water solubility, and thus there is a fear that when the composition is used as a preparation for oral administration, dissolution and absorption of the physiologically active substance in the small intestine and thereafter are insufficient, a pH adjusting agent or other solubilizing aids may be added for the purpose of controlling the dissolution behavior of the composition. With the use of pH adjusting agent or the like, it is possible to reduce any change in the drug dissolution property due to the environmental pH. Further, since individual patients may have different in vivo pH values, in order to obtain uniform effect in various patients, reduction of change in the drug dissolution property due to environmental pH is significantly meaningful.

Examples of the pH adjusting agent include organic acids such as citric acid, tartaric acid, adipic acid, ascorbic acid, malic acid, fumaric acid, malonic acid, succinic acid, maleic acid, aspartic acid, glutamic acid, etc. or salts thereof (e.g., sodium dihydrogen citrate, disodium citrate, calcium citrate, monosodium fumarate, monosodium succinate, sodium aspartate, magnesium aspartate, arginine glutamate, potassium glutamate, sodium glutamate, etc.), inorganic acids such as phosphoric acid, hydrochloric acid, sulfuric acid, etc. and salts thereof (e.g., potassium dihydrogen phosphate, sodium dihydrogen phosphate, etc.), acidic polymers such as carboxyvinyl polymer, etc. and salts thereof. Among these, citric acid, tartaric acid, fumaric acid, ascorbic acid, aspartic acid, glutamic acid and salts thereof, and the like are preferred. In addition, examples of the other solubilizing aids include cyclodextrins such as β-cyclodextrin, maltosyl-β-cyclodextrin, etc., surfactants such as Polysorbate 80, glycerin monostearate, etc., polyethylene glycols such as Polyethylene Glycol 4000, Polyethylene Glycol 6000, etc., and the like.

The content of the pH adjusting agent or the other solubilizing aid varies depending on the kind and content of the physiologically active substance, the size of the composition or the like, but it is, for example, from 1 to 50% by weight, and preferably from 5 to 40% by weight.

In Method 1 of the dissolution test in the Japanese Pharmacopoeia (rotating basket method, rotation speed 125 rpm, 37° C.) using a phosphate buffer (1000 mL) containing sodium dodecyl sulfate at 0.5%, the above-mentioned granule containing a physiologically active substance and a hydrophilic polymer shows the dissolution rate of a physiologically active substance from a controlled release composition at 45 min after the start of the test is not less than 70%, preferably not less than 80%, more preferably not less than 90%.

As the above-mentioned granule containing a physiologically active substance and a hydrophilic polymer, a plain granule wherein a core particle is coated with a coating layer containing the above-mentioned physiologically active substance and a hydrophilic polymer is preferable.

Examples of the core particle include inert carrier particle, and specifically, a core particle produced from sucrose, lactose, starch, microcrystalline cellulose, waxes and the like is used.

The core particle preferably has an average particle size of about 100 μm-about 1,500 μm, preferably about 500 μm-about 700 μm.

While the content of the core particle in the controlled release capsule preparation of the present invention varies depending on the content of the physiologically active substance, size of the preparation, kind of the core particle and the like, it is, for example, about 1 to about 70 wt %, preferably about 1 to about 50 wt %, more preferably about 1 to about 30 wt %.

The plain granule can also be prepared, for example, by a rolling granulation method, a pan coating method, a fluidized bed coating method, a molten granulation method, an extrusion/marumerization method and the like wherein the above-mentioned physiologically active substance and a hydrophilic polymer (e.g., hydroxypropylcellulose (e.g., HC-SSL, HPC-SL, HPC-SL-T and the like), hydroxypropylmethylcellulose (e.g., TC-5-RW, TC-5-EW and the like)), or a mixture thereof with a binder, an excipient (e.g., D-mannitol, microcrystalline cellulose), a disintegrant (e.g., croscarmellose sodium, microcrystalline cellulose, low-substituted hydroxypropylcellulose (e.g., L-HPC-32 and the like) and the like) and the like, which are dissolved or dispersed in a suitable solvent such as water, lower alcohol (e.g., methanol, ethanol and the like) and the like, to be used as a coating agent on a core particle is sprayed as a solution or suspension or added as a powder by a small amount.

Particularly, in the plain granule, a core particle is preferably coated with the above-mentioned coating agent containing the physiologically active substance and the hydrophilic polymer using a rotating blade fluidizing granulator. In this case, the following conditions are preferably employed.
(i) adhesion to a nozzle of the rotating blade fluidizing granulator is prevented,
(ii) drying conditions: inlet air temperature is 55 to 75° C., preferably 60 to 70° C., and inlet air flow is generally 1.0 to 3.0 m$^3$/min, preferably 1.5 to 2.5 m$^3$/min, per 3.5 L of effective capacity of the rotating blade fluidizing granulator,
(iii) temperature conditions: product temperature is 25 to 35° C., preferably 25 to 30° C.,
(iv) humidity conditions: exhaustion humidity is 60 to 95% RH, preferably 60 to 90% RH, more preferably 70 to 80% RH, and
(v) spray rate: spray rate is generally 20 to 40 g/min, preferably 25 to 35 g/min, per 3.5 L of effective capacity of the rotating blade fluidizing granulator.

A method of preventing adhesion to a nozzle of a rotating blade fluidizing granulator includes periodical cleaning during the step, use of auxiliary air and the like.

By setting these conditions, superior property of difficult agglomeration is conferred on the obtained plain granule.

When a granule is produced by coating a core particle with a coating agent comprising a physiologically active substance and a disintegrant using a rotating blade fluidizing granulator, the following conditions can be set.
(i) humidity conditions: exhaustion humidity is 60 to 95% RH, preferably 60 to 90% RH, more preferably 70 to 80% RH, and
(ii) the disintegrant is croscarmellose sodium and (or) microcrystalline cellulose.

More preferably, the following conditions are set.
(i) adhesion to a nozzle of the rotating blade fluidizing granulator is prevented,
(ii) drying conditions: inlet air temperature is 55 to 75° C., preferably 60 to 70° C., and inlet air flow is 1.0 to 3.0 m$^3$/min, preferably 1.5 to 2.5 m$^3$/min per 3.5 L of effective capacity of the rotating blade fluidizing granulator.
(iii) temperature conditions: product temperature is 25 to 35° C., preferably 25 to 30° C.
(iv) humidity conditions: exhaustion humidity is 60 to 95% RH, preferably 60 to 90% RH, more preferably 70 to 80% RH.

(v) spray rate: spray rate is 20 to 40 g/min, preferably 25 to 35 g/min per 3.5 L of effective capacity of the rotating blade fluidizing granulator.

(vi) the disintegrant is croscarmellose sodium and (or) microcrystalline cellulose.

By setting the above-mentioned conditions, the following effects can be provided.

(1) Production time of the granule can be increased.

(2) Even when the granule is produced in a rotating blade fluidizing granulator at high chamber humidity, the dissolution property of the physiologically active substance from a granule or a pharmaceutical composition containing same (e.g., controlled release capsule preparation) is superior.

By setting the above-mentioned conditions, moreover, the method is applicable to a physiologically active substance other than the compound represented by the formula (I)-A, a prodrug thereof and a salt thereof.

Such physiologically active substance may be any of a solid, powder, crystal, oil, solution and the like. Examples thereof include one or more components selected from a nutritional supplement, an antipyretic analgesic anti-inflammatory agent, a psychotropic agent, an antianxiety drug, an antidepressant, a sedative-hypnotic agent, an anticonvulsant, a central nervous system agent, a brain metabolic improver, a cerebral circulation improver, an antiepilepsy drug, a sympathomimetic, a digestive medicine, an antacid, an antiulcerogenic drug, an antitussive expectorant, an antiemetic, an anapnoic, a bronchodilator, an antiallergic agents, a dental and oral drug, an antihistamine agent, a cardiotonic, an antiarrhythmic drug, a diuretic, an antihypertensive agent, a vasoconstrictor, a colonary vasodilator, a peripheral vasodilator, a hypolipidemic, a cholagogue, an antibiotic, a chemotherapeutic agent, a diabetic drug, a drug for osteoporosis, an antirheumatic drug, a skeleton muscle relaxant, a spasmolytic, a hormone preparation, a narcotic alkaloid, a sulfa drug, a therapeutic drug for gout, a blood coagulation inhibitor, an antimalignant tumor agent, a therapeutic drug for Alzheimer's disease and the like.

Examples of the nutritional supplement include vitamins such as vitamin A, vitamin D, vitamin E (acetic acid d-α-tocopherol and the like), vitamin $B_1$ (dibenzoylthiamine, fursultiamine hydrochloride and the like), vitamin $B_2$ (riboflavin butyrate and the like), vitamin $B_6$ (pyridoxine hydrochloride and the like), vitamin C (ascorbic acid, sodium L-ascorbate and the like), vitamin $B_{12}$ (hydroxocobalamin acetate, cyanocobalamin and the like), minerals such as calcium, magnesium, iron and the like, a protein, an amino acid, an oligosaccharide, a natural medicine and the like.

Examples of the antipyretic analgesic anti-inflammatory agent include aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, serrapeptase, lysozyme chloride, tolfenamic acid, mefenamic acid, diclofenac sodium, flufenamic acid, salicylamide, aminopyrine, ketoprofen, indomethacin, bucolome, pentazocine and the like.

Examples of the psychotropic agent include chlorpromazine, reserpine and the like.

Examples of the antianxiety drug include alprazolam, chlordiazepoxide, diazepam and the like.

Examples of the antidepressant include imipramine, maprotiline hydrochloride, amphetamine and the like.

Examples of the sedative-hypnotic agent include estazolam, nitrazepam, diazepam, perlapine, phenobarbital sodium and the like.

Examples of the anticonvulsant include scopolamine hydrobromide, diphenhydramine hydrochloride, papaverine hydrochloride and the like.

Examples of the central nervous system agent include citicoline and the like.

Examples of the brain metabolic improver include meclofenoxate hydrochloride and the like.

Examples of the cerebral circulation improver include vinpocetine and the like.

Examples of the antiepilepsy drug include phenyloin, carbamazepine and the like.

Examples of the sympathomimetic include isoproterenol hydrochloride and the like.

Examples of the digestive medicine include stomachics and digestives such as diastase, saccharated pepsin, scopolia extract, cellulase AP3, lipase AP, cassia oil and the like, antiflatulent such as berberine chloride, resistant lactobacilli, bifidobacteria and the like, and the like.

Examples of the antacid include magnesium carbonate, sodium hydrogencarbonate, magnesium aluminometasilicate, synthetic hydrotalcite, precipitated calcium carbonate, magnesium oxide and the like.

Examples of the antiulcerogenic drug include lansoprazole, omeprazole, rabeprazole, pantoprazole, famotidine, cimetidine, ranitidine hydrochloride and the like.

Examples of the antitussive expectorant include cloperastine hydrochloride, dextromethophan hydrobromide, theophylline, potassium guaiacolsulfonate, guaifenesin, codeine phosphate and the like.

Examples of the antiemetic include difenidol hydrochloride, metoclopramide and the like.

Examples of the anapnoic include levallorphan tartrate and the like.

Examples of the bronchodilator include theophylline, salbutamol sulfate and the like.

Examples of the antiallergic agent include amlexanox, seratrodast and the like.

Examples of the dental and oral drug include oxytetracycline, triamcinolone acetonide, chlorhexidine hydrochloride, lidocaine and the like.

Examples of the antihistamine agent include diphenhydramine hydrochloride, promethazine, isothipendyl hydrochloride, dl-chlorpheniramine maleate and the like.

Examples of the cardiotonic include caffeine, digoxin and the like.

Examples of the antiarrhythmic drug include procaineamide hydrochloride, propranolol hydrochloride, pindolol and the like.

Examples of the diuretic include thiazide such as isosorbide, furosemide, HCTZ and the like, and the like.

Examples of the antihypertensive agent include delapril hydrochloride, captopril, hexamethonium bromide, hydralazine hydrochloride, labetalol hydrochloride, manidipine hydrochloride, candesartan cilexetil, methyldopa, losartan, valsartan, eprosartan, irbesartan, tasosartan, telmisartan and the like.

Examples of the vasoconstrictor include phenylephrine hydrochloride and the like.

Examples of the coronary vasodilator include carbochromene hydrochloride, molsidomine, verapamil hydrochloride and the like.

Examples of the peripheral vasodilators include cinnarizine and the like.

Examples of the hypolipidemic include cerivastatin sodium, simvastatin, pravastatin sodium and the like.

Examples of the cholagogue include dehydrocholic acid, trepibutone and the like.

Examples of the antibiotic include cephem antibiotics such as cefalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil, cefotiam hydrochloride, cefozopran hydrochloride, cefinenoxime hydrochloride, cefsulodin sodium and the like, synthetic antibacterial agents such as ampicillin, ciclacillin, sulbenicillin sodium, naldixic acid, enoxacin and the like, monobactum, penem and carbapenem antibiotics such as carumonam sodium and the like, and the like.

Examples of the chemotherapeutic agent include sufamethizol, sufamethizol hydrochloride, thiazosulfone and the like.

Examples of the diabetic drug include tolbutamide, pioglitazone hydrochloride, glibenclamide, troglitazone, rosiglitazone maleate, acarbose, miglitol, emiglitate and the like.

Examples of the drug for osteoporosis include ipriflavone and the like.

Examples of the skeleton muscle relaxant include methocarbamol and the like.

Examples of the spasmolytic include meclizine hydrochloride, dimenhydrinate and the like.

Examples of the antirheumatic drug include methotrexate, bucillamine and the like.

Examples of the hormone preparation include liothyronine sodium, dexamethazone sodium phosphate, prednisolone, oxendolone, leuprorelin acetate and the like.

Examples of the narcotic alkaloid include opium, morphine hydrochloride, ipecic, oxycodon hydrochloride, opium alkaloid hydrochloride, cocaine hydrochloride and the like.

Examples of the sulfa drug include sulfamine, sulfisomidine, sufamethizol and the like.

Examples of the therapeutic drug for gout include allopurinol, colchicine and the like.

Examples of the blood coagulation inhibitor include dicoumarol.

Examples of the anti-malignant tumor agent include 5-fluorouracil, uracil, mitomycin and the like.

Examples of the therapeutic agents for Alzheimer's disease include idebenone, vinpocetine and the like.

Moreover, the effect of the controlled release, capsule preparation of the present invention can be further enhanced by combining a compound represented by the formula (I)-Aa or a prodrug thereof or a salt thereof with a physiologically active substances having other efficacy. Examples of the physiologically active substances having other efficacy include "sexual hormone drugs (hormone-based drugs)", "alkylating agents", "antimetabolites", "anticancerous antibiotics", "plant alkaloids", "immunotherapeutic agents", "drugs inhibiting the action of cell growth factors and their receptors" and the like (hereinafter, abbreviated as combination drugs). The combination drugs can be used as different pharmaceutical compositions, or can be used in a mixed preparation prepared by adding them to the above-described controlled release capsule preparation.

Examples of the "sex hormone agent" include fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, antiestrogen (e.g., tamoxifen citrate, toremifene citrate etc.), ER down-regulator (for example, fulvestrant etc.), human postmenopausal gonadotropin, follitropin, pill preparation, mepitiostane, testolactone, aminoglutethimide, LHRH receptor modulator [LH-RH receptor agonist (e.g., goserelin acetate, buserelin acetate, leuprorelin acetate etc.), LH-RH receptor antagonist (e.g., ganirelix, cetrorelix, abarelix etc.)], droloxifene, epitiostanol, ethinylestradiol sulfonate, aromatase inhibitor (e.g., fadrozole hydrochloride, anastrozole, retrozole, exemestane, vorozole, formestane etc.), anti-androgen (e.g., flutamide, bicartamide, nilutamide etc.), 5α-reductase inhibitor (e.g., finasteride, dutasteride, epristeride etc.), corticosteroid (e.g., cortisol, dexamethasone, prednisolone, betamethasone, triamcinolone etc.), androgen synthesis inhibitor (e.g., abiraterone etc.), retinoid and drugs that retard retinoid metabolism (e.g., liarozole etc.) and the like.

Examples of the "alkylating agent" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin and the like.

Examples of the "antimetabolite" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, etc.), aminopterine, leucovorin calcium, tabloid, butocine, calcium folinate, calcium levofolinate, cladribine, fludarabine, gemcitabine, hydroxycarbamide, pentostatin, piritrexim, idoxuridine, mitoguazone, thiazophrine and the like.

Examples of the "anticancerous antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride and the like.

Examples of the "plant alkaloid" include etoposide, etoposide phosphate, vinblastine sulfate, vincristine sulfate, vindesine sulfate, teniposide, paclitaxel, docetaxel, vinorelbine and the like.

Examples of the "immunotherapeutic agent (BRM)" include picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole and the like.

The "cell growth factor" in the phrase "drugs inhibiting the action of cell growth factors and their receptors" may be any substance which promotes cell proliferation and may be exemplified by peptides having a molecular weight of 20,000 or less, which are factors exhibiting their action at low concentrations by binding to a receptor. Specific examples thereof include (1) EGF (epidermal growth factor) or substances having substantially identical activity therewith [for example, EGF, heregulin (HER2 ligand), etc.], (2) insulin or substances having substantially identical activity therewith [for example, insulin, IGF (insulin-like growth factor)-1, IGF-2, etc.], (3) FGF (fibroblast growth factor) or substances having substantially identical activity therewith [for example, acidic FGF, basic FGF, KGF (keratinocyte growth factor), FGF-10, etc.], (4) other cell growth factors [for example, CSF (colony stimulating factor), EPO (erythropoietin), IL-2 (interleukin-2), NGF (nerve growth factor), PDGF (plateletderived growth factor), TGF β (transforming growth factor β), HGF (hepatocyte growth factor), VEGF (vascular endothelial growth factor), etc.], and the like.

The "receptor for cell growth factor" may be any receptor capable of binding to the above-mentioned cell growth factors, and specific examples thereof include an EGF receptor, HER2 (heregulin receptor), an insulin receptor, an IGF receptor, a FGF receptor-1 or a FGF receptor-2, and the like.

The "drug inhibiting the action of cell growth factors" may be exemplified by antibodies against cell growth factors and their receptors such as antibody against VEGF (e.g., bevacizumab), antibody against VEGF receptor, EGF receptor antibodies including cetuximab; HER2 antibodies including Herceptin and the like; tyrosine kinase inhibitors such as gefitinib, erlotinib (EGF receptor tyrosine kinase inhibitor), GW2016 (EGF receptor/HER2 tyrosine kinase inhibitor), and the compounds described in WO98-03505A and WO01-77107A (HER2 tyrosine kinase inhibitor) and the like; a ribozyme, antisense drugs, siRNA drugs, each of which inhibits expression of cell growth factors or their receptors; or the like.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, etc.), topoisomerase II inhibitors (e.g., sobuzoxane, etc.), differentiation inducers (e.g., retinoid, vitamin D, etc.), angiogenesis inhibiting drugs (e.g., thalidomide, SU11248 etc.), serine/threonine kinase inhibitor, endothelin receptor antagonists (e.g., atrasentan etc.), proteasome inhibitors (e.g., bortezomib etc.), Hsp90 inhibitors (e.g., 17-AAG etc.), spironolactone, minoxidil, 11α-hydroxyprogesterone, bone resorption inhibitory metastasis suppressing agents (e.g., zoledronic acid, alendronic acid, pamidronic acid, etidronic acid, ibandronic acid, clodronic acid), α1-blockers (e.g., tamsulosin, naftopidil, urapidil, alfuzosin, terazosin, prazosin, silodosin etc.), and the like can also be used.

The combination drugs are preferably LHRH receptor modulating drugs (LHRH modulators) [for example, LHRH receptor agonists (e.g., goserelin acetate, buserelin acetate, leuprorelin acetate, etc.) or LHRH receptor antagonists (e.g., ganirelix, cetrorelix, abarelix, etc.)], and can be used in combination with these, so as to remove androgen or estrogen in blood more effectively.

Dosage of the combination drugs can be appropriately selected based on the amounts that are clinically used. Further, the mixing ratio of the physiologically active substance and combination drugs in the controlled release capsule preparation of the invention can be appropriately selected in accordance with the subjects to be administered, diseases to be treated, symptoms, combinations or the like. For example, when the subject to be administered is a human, the combination drug may be used in an amount of about 0.01 to 100 parts by weight with respect to 1 part by weight of the aforementioned physiologically active substance.

While the content of a concomitant drug in the controlled release capsule preparation of the present invention varies depending on the kind of the physiologically active substance and concomitant drug, size of the preparation and the like, it is, for example, about 1 to about 90 wt %, preferably about 5 to about 85 wt %, more preferably about 10 to about 80 wt %, and particularly preferably about 20 to about 40 wt %.

An enteric granule can be obtained by coating the above-mentioned granule containing a physiologically active substance and a hydrophilic polymer, preferably a granule wherein a core particle is coated with the above-mentioned physiologically active substance and a hydrophilic polymer (hereinafter sometimes to be abbreviated as a plain granule thereof), with a coating layer containing an enteric coating agent.

The enteric coating agent is a pharmaceutically acceptable polymer and is not particularly limited, as long as it can form a film structure having the function of controlling release of the above-mentioned physiologically active substance. There is no particular limitation on the kind of the controlled release film as well, and examples thereof include (1) a film which has relatively large micropores as can be seen in porous films and controls release of the content through the micropores, (2) a non-porous film in a film form, which controls release of the content by diffusion through the interstices between molecular chains resulting from the motion of the film-forming polymers, (3) a film which controls release of the content as a result of dissolution or decomposition of the film, and the like. In the case of the above-mentioned (1) or (2), for example, polymers which are insoluble or sparingly soluble in water can be used as the coating polymer, and in the case of (3), for example, polymers exhibiting pH-dependent or delayed-dissolution type water solubility can be used.

The polymer exhibiting pH-dependent water solubility is preferably a polymer having an acidic dissociating group, for example, which is insoluble or sparingly soluble in an acidic (pH 1 to 3) medium such as gastric juice, and is soluble in a medium in a pH range of weakly acidic to weakly alkaline (pH 5 to 8) such as intestinal juice. Examples of such polymer exhibiting pH-dependent water solubility include cellulose acetate phthalate, hydroxypropylmethylcellulose phthalate, hydroxymethylcellulose acetate succinate, methacrylic acid copolymers (methacrylic acid-methyl acrylate copolymers, methacrylic acid-ethyl acrylate copolymers, etc., for example, Eudragit L100-55 (dried methacrylic acid copolymers LD), Eudragit L30D-55 (methacrylic acid copolymers LD), Eudragit L100 (methacrylic acid copolymers L), Eudragit S100 (methacrylic acid copolymers S), FS (tradenames, Röhm-Pharma GmbH)) and the like, which are used as enteric coating agents. These polymers may be used in mixtures of two or more species at appropriate ratios.

Specific examples of the polymer exhibiting delayed-dissolution type water solubility include hydroxypropylcellulose (HPC) such as HPC-SSL (tradename, Nippon Soda Co., Ltd.) (viscosity of 2 wt % aqueous solution at 20° C.: 2.0 to 2.9 mPa·s), HPC-SL (tradename, Nippon Soda Co., Ltd.) (viscosity of 2 wt % aqueous solution at 20° C., 3.0 to 5.9 mPa·s), HPC-SL-T (tradename, Nippon Soda Co., Ltd.) (viscosity of 2 wt % aqueous solution at 20° C.: 1.2 to 3.7 mPa·s), HPC-L (tradename, Nippon Soda Co., Ltd.) (viscosity of 2 wt % aqueous solution at 20° C., 6.0 to 10.0 mPa·s), HPC-M (tradename, Nippon Soda Co., Ltd.) (viscosity of 2 wt % aqueous solution at 20° C.: 150 to 400 mPa·s), HPC-H (tradename, Nippon Soda Co., Ltd.) (viscosity of 2 wt % aqueous solution at 20° C.: 1000 to 4000 mPa·s), or the like;

hydroxypropylmethylcellulose such as TC-5E (tradename, Shin-Etsu Chemical Co., Ltd.) (viscosity of 2 wt % aqueous solution at 20° C.: about 3 mPa·s), TC-5-EW (tradename, Shin-Etsu Chemical Co., Ltd.) (viscosity of 2 wt % aqueous solution at 20° C.: about 3 mPa·s), SB-4 (tradename, Shin-Etsu Chemical Co., Ltd.) (viscosity of 2 wt % aqueous solution at 20° C.: about 4 mPa·s), TC-5MW (tradename, Shin-Etsu Chemical Co., Ltd.) (viscosity of 2 wt % aqueous solution at 20° C.: about 4.5 mPa·s), TC-5R (tradename, Shin-Etsu Chemical Co., Ltd.) (viscosity of 2 wt % aqueous solution at 20° C.: about 6 mPa·s), TC-5-RW (tradename, Shin-Etsu Chemical Co., Ltd.) (viscosity of 2 wt % aqueous solution at 20° C.: about 6 mPa·s), TC-5S (tradename, Shin-Etsu Chemical Co., Ltd.) (viscosity of 2 wt % aqueous solution at 20° C.: about 15 mPa·s), Metolose 60SH-50 (tradename, Shin-Etsu Chemical Co., Ltd.) (viscosity of 2 wt % aqueous solution at 20° C.: about 50 mPa·s), Metolose 65SH-50 (tradename, Shin-Etsu Chemical Co., Ltd.) (viscosity of 2 wt % aqueous solution at 20° C.: about 50 mPa·s), Metolose 90SH-100 (tradename, Shin-Etsu Chemical Co., Ltd.) (viscosity of 2 wt % aqueous solution at 20° C.: about 100 mPa·s), Metolose 65SH-400 (tradename, Shin-Etsu Chemical Co., Ltd.) (viscosity of 2 wt % aqueous solution at 20° C.: about 400 mPa·s), Metolose 90SH-400 (tradename, Shin-Etsu Chemical Co., Ltd.) (viscosity of 2 wt % aqueous solution at 20° C.: about 400 mPa·s), Metolose 65SH-1500 (tradename, Shin-Etsu Chemical Co., Ltd.) (viscosity of 2 wt % aqueous solution at 20° C.: about 1500 mPa·s), Metolose 60SH-4000 (tradename, Shin-Etsu Chemical Co., Ltd.) (viscosity of 2 wt % aqueous solution at 20° C.: about 4000 mPa·s), Metolose 65SH-4000 (tradename, Shin-Etsu Chemical Co., Ltd.) (viscosity of 2 wt % aqueous solution at 20° C.: about 4000 mPa·s), Metolose 90SH-4000 (tradename, Shin-Etsu Chemical Co., Ltd.) (viscosity of 2 wt % aqueous solution at 20° C.: about 4000 mPa·s), Metolose 90SH-30000 (tradename, Shin-Etsu Chemical Co., Ltd.) (viscosity of 2 wt % aqueous solution at 20° C.: about 30000 mPa·s), or the like;

methylcellulose such as Metolose SM15 (tradename, Shin-Etsu Chemical Co., Ltd.) (viscosity of 2 wt % aqueous solution at 20° C.: about 15 mPa·s), Metolose SM25 (tradename, Shin-Etsu Chemical Co., Ltd.) (viscosity of 2 wt % aqueous solution at 20° C.: about 25 mPa·s), Metolose SM100 (tradename, Shin-Etsu Chemical Co., Ltd.) (viscosity of 2 wt % aqueous solution at 20° C.: about 100 mPa·s), Metolose SM400 (tradename, Shin-Etsu Chemical Co., Ltd.) (viscosity of 2 wt % aqueous solution at 20° C.: about 400 mPa·s), Metolose SM1500 (tradename, Shin-Etsu Chemical Co., Ltd.) (viscosity of 2 wt % aqueous solution at 20° C.: about 1500 mPa·s), Metolose SM4000 (tradename, Shin-Etsu Chemical Co., Ltd.) (viscosity of 2 wt % aqueous solution at 20° C.: about 4000 mPa·s), Metolose SM8000 (tradename, Shin-Etsu Chemical Co., Ltd.) (viscosity of 2 wt % aqueous solution at 20° C.: about 8000 mPa·s), or the like;

polyethylene oxide such as WSR N-12K (tradename, Union Carbide Corp.) (viscosity of 2 wt % aqueous solution at 20° C.: 400 to 800 mPa·s), WSR N-60K (tradename, Union Carbide Corp.) (viscosity of 2 wt % aqueous solution at 20° C.: 2000 to 4000 mPa·s), WSR 301 (tradename, Union Carbide Corp.) (viscosity of 1 wt % aqueous solution at 25° C.: 1500 to 4500 mPa·s), WSR Coagulant (tradename, Union Carbide Corp.) (viscosity of 1 wt % aqueous solution at 25° C.: 4500 to 7500 mPa·s), WSR 303 (tradename, Union Carbide Corp.) (viscosity of 1 wt % aqueous solution at 25° C.: 7500 to 10000 mPa·s), WSR 308 (tradename, Union Carbide Corp.) (viscosity of 1 wt % aqueous solution at 25° C.: 10000 to 15000 mPa·s), or the like;

sodium carboxymethylcellulose such as Sanlose F-150MC (tradename, Nippon Paper Group, Inc.) (viscosity of 1 wt % aqueous solution at 25° C.: 1200 to 1800 mPa·s), Sanlose F-300MC (tradename, Nippon Paper Group, Inc.) (viscosity of 1 wt % aqueous solution at 25° C.: 2500 to 3000 mPa·s), Sanlose F-1000MC (tradename, Nippon Paper Group, Inc.) (viscosity of 1 wt % aqueous solution at 25° C.: 8000 to 12000 mPa·s), or the like;

low-substituted hydroxypropylcellulose such as LH-11 (tradename, Shin-Etsu Chemical Co., Ltd.), LH-21 (tradename, Shin-Etsu Chemical Co., Ltd.), LH-31 (tradename, Shin-Etsu Chemical Co., Ltd.), LH-22 (tradename, Shin-Etsu Chemical Co., Ltd.), LH-32 (tradename, Shin-Etsu Chemical Co., Ltd.), LH-20 (tradename, Shin-Etsu Chemical Co., Ltd.), LH-30 (tradename, Shin-Etsu Chemical Co., Ltd.), or the like; and the like. Preferably, it is a polymer whose viscosity of a 2 wt % aqueous solution at 20° C. or viscosity of a 1 wt % aqueous solution at 25° C. is not lower than 10 mPa·s. These polymers may be used in mixtures of two or more species at appropriate ratios.

The polymer which is insoluble or sparingly soluble in water includes block polymers and copolymers. The polymer which is insoluble or sparingly soluble in water refers to a polymer whose water solubility at 37° C. is less than 0.1 mg/mL. The polymer is exemplified by lipophilic bases such as carnauba wax, hydrogenated castor oil, hydrogenated rapeseed oil and polyglycerols; cellulose esters, acrylic polymers, polyvinyl acetate, polyvinyl chloride, compositions having at least one component selected from the aforementioned polymers, or mixtures thereof. Also, it includes, for example, polyvinyl acetate, polymethyl methacrylate, poly(vinyl chloride, vinyl alcohol, vinyl acetate) (terpolymer of vinyl chloride, vinyl alcohol and vinyl acetate) or the like. Further, it includes, for example, ethylcellulose, cellulose acetate, cellulose acetate butyrate, cellulose acetate propionate, nitrocellulose, polymethyl methacrylate, poly(ethyl acrylate, methyl methacrylate) (for example, Eudragit NE (tradename, Röhm-Pharma GmbH)), polyethylene, polyisobutylene, poly(ethyl acrylate, methyl methacrylate, trimethylammonioethyl methacrylate chloride (for example, Eudragit RS, RL (tradenames, Röhm-Pharma GmbH)), compositions having at least one component selected from the aforementioned polymers, or mixtures thereof. However, the polymer is not limited to these. Commercially available latex, pseudolatex and polymer emulsions can be also used in coating.

In a preferred embodiment of the invention, the enteric coating agent is a methacrylic acid-methyl acrylate copolymer or a methacrylic acid-ethyl acrylate copolymer, particularly Eudragit L100 (methacrylic acid copolymer L), Eudragit S100 (methacrylic acid copolymer S). Particularly, a combined use of Eudragit L100 (methacrylic acid copolymer L) and Eudragit S100 (methacrylic acid copolymer S) at a ratio of 1:2-1:4, preferably 1:3, is preferable.

Furthermore, in another preferred embodiment of the invention, the enteric coating agent is poly(ethyl acrylate, methyl methacrylate, trimethylammonioethyl methacrylate chloride).

In order to adjust the softening temperature of the polymer, a lubricant, a plasticizer and the like may be added to the enteric coating agent. The softening temperature is an important factor for controlling mechanical properties of a polymer.

Examples of the lubricant include magnesium stearate, calcium stearate, talc, colloidal silica, synthetic aluminum silicate, magnesium aluminometasilicate and the like. Of these, talc is preferable.

Suitable examples of the plasticizer include acetyl tributyl citrate, acetyl triethyl citrate, castor oil, diacetylated monoglyceride, dibutyl sebacate, diethyl phthalate, glycerin, mono- and diacetylated monoglyceride, polyethylene glycol, propylene glycol, triacetin, triethyl citrate and the like. Of these, triethyl citrate is preferable.

The average particle size of enteric granule is preferably about 50 μm to about 2000 μm, and more preferably is about 100 μm to about 1400 μm.

The enteric granule is prepared by coating a plain granule with an aqueous dispersion or non-aqueous solution containing an enteric coating agent (hereinafter sometimes to be referred to as "enteric coating solution"), which is followed by drying. Alternatively, the granule is also prepared by compression-molding the coating agent, etc. on the periphery of the plain granule to form a coating layer, for example, using the same conventional methods in the art of preparation technology as in the preparation of a multilayer tablet or a core-containing tablet.

Examples of the method for coating a plain granule with an enteric coating solution include the method including spray coating and the like.

The amount of the enteric coating layer after drying is about 0.01% to about 500% by weight, preferably about 0.1% to about 300% by weight, and more preferably about 1% to about 200% by weight, relative to the plain granule.

In addition, the film thickness of the enteric coating layer is about 1 µm to about 10 mm, and preferably about 5 µm to about 5 mm.

As the solvent for the enteric coating solution, water or an organic solvent can be used individually or as a mixed solvent of the two. When a mixed solvent is to be used, the mixing ratio of water and organic solvent (water/organic solvent: weight ratio) may vary within the range of 1 to 100%. The organic solvent is not particularly limited as long as it dissolves the coating polymer, and one used for the production of the above-mentioned plain granule, preferably, lower alcohol (e.g., methanol, ethanol and the like) is used. However, water or a mixed solvent of water and an organic solvent is more preferably used. In this case, where necessary, an acid such as tartaric acid, citric acid, succinic acid, fumaric acid or maleic acid may be added to the enteric coating solution as a stabilizing agent.

In the case of coating by spray coating, the operation can be performed according to the general coating methods, and specifically, a plain granule is spray-coated with an enteric coating solution according to, for example, a fluidized bed coating method, a pan coating method or the like, where use of a rotating blade fluidizing granulator for the coating is preferable. In this case, where necessary, a lubricant such as talc, titanium oxide, magnesium stearate, calcium stearate or the like, or a plasticizer such as glycerin fatty acid ester, hydrogenated castor oil, triethyl citrate, cetyl alcohol, stearyl alcohol or the like may be added to an enteric coating solution.

After coating, if needed, an antistatic agent such as talc may be mixed as well.

In the enteric coating solution, at least one ionic, nonionic or polymeric surfactant may be added as a stabilizing agent. Suitable examples of the surfactant include diethanolamine, fatty acids, hydroxypropylmethylcellulose, hydroxypropylcellulose, monoethanolamine, nonoxynol, octoxynol, oleic acid, Poloxamers, polyoxyethylene 50 stearate, polyoxy fatty acids, polyoxyl hydrocarbon ethers, polysorbates (e.g., Polysorbate 80, etc.), povidone, fatty acid salts, sodium lauryl sulfate, sorbitan esters, trolamine and the like, but are not limited to these.

While the content of the enteric coating agent in the controlled release capsule preparation of the present invention varies depending on the kind of the physiologically active substance, kind of the enteric coating agent, size of the preparation and the like, it is, for example, about 1 to about 80 wt %, preferably about 1 to about 50 wt %, more preferably about 10 to about 30 wt %.

While the content of the lubricant and/or plasticizer and the like in the coating layer of the controlled release capsule preparation of the present invention varies depending on the content of the physiologically active substance, kind of the lubricant and/or plasticizer and the like, size of the preparation and the like, it is, for example, about 1 to about 60 wt %, preferably about 1 to about 40 wt %, more preferably about 1 to about 20 wt %, relative to the whole release controlled capsule preparation.

By coating a plain granule with a coating layer containing the above-mentioned enteric coating agent using the above-described methods, immediate dissolution of the physiologically active substance from the enteric granule at acidic pH (e.g., pH 1 to 3), which corresponds to dissolution in the vicinity of the stomach during the early stage after oral administration, is suppressed, and subsequent dissolution of the physiologically active substance at weakly acidic to weakly alkaline pH (e.g., pH 5 to 8), which corresponds to dissolution in the small intestine and thereafter, especially in the duodenum to ileum, is sustained for a long time. In particular, it is possible to more strictly control the dissolution during the early stage after administration, by means of the controlled release film.

Specifically, in the enteric granule, 1) according to Method 2 of the dissolution test in the Japanese Pharmacopoeia (paddle method, rotation speed of paddle: 50 rpm, 37° C.) using 900 mL of $1^{st}$ fluid for the disintegration test in the Japanese Pharmacopoeia, the dissolution rate of the physiologically active substance from the controlled release composition at 15 minutes after initiation of the test is less than 10%, preferably less than 5% and more preferably less than 3%; and 2) according to Method 2 of the dissolution test in the Japanese Pharmacopoeia (paddle method, rotation speed of paddle: 50 rpm, 37° C.) using 900 mL of $2^{nd}$ fluid for the disintegration test in the Japanese Pharmacopoeia, the dissolution rate of the physiologically active substance from the controlled release composition at 24 hours after initiation of the test is 70% or more, preferably is 80% or more and more preferably is 90% or more.

Specifically, the enteric granule of the present invention comprises a plain granule wherein a core particle is coated with a coating layer containing (1) the above-mentioned physiologically active substance, (2) a hydrophilic polymer selected from the group consisting of hydroxypropylcellulose, hydroxypropylmethylcellulose, methylcellulose, polyethylene oxide, sodium carboxymethylcellulose and low-substituted hydroxypropylcellulose (preferably, hydroxypropylcellulose, hydroxypropylmethylcellulose), (3) an excipient selected from the group consisting of lactose, sucrose, D-mannitol, D-sorbitol, starch, pregelatinized starch, dextrin, microcrystalline cellulose, low-substituted hydroxypropylcellulose, sodium carboxymethylcellulose, gum arabic, dextrin, pullulan, synthetic aluminum silicate and magnesium aluminometasilicate (preferably, D-mannitol, microcrystalline cellulose), and (4) a disintegrant selected from the group consisting of lactose, sucrose, starch, carboxymethylcellulose, calcium carboxymethylcellulose, croscarmellose sodium, microcrystalline cellulose, sodium carboxymethyl starch and low-substituted hydroxypropylcellulose (preferably, croscarmellose sodium, microcrystalline cellulose, low-substituted hydroxypropylcellulose and the like, particularly preferably croscarmellose sodium, microcrystalline cellulose), wherein the plain granule is coated with a coating layer containing (5)(a) an enteric coating agent selected from the group consisting of cellulose acetate phthalate, hydroxypropylmethylcellulose phthalate, hydroxymethylcellulose acetate succinate and methacrylic acid copolymers and preferably methacrylic acid copolymers (preferably, methacrylic acid copolymer), (b) a lubricant selected from the group consisting of magnesium stearate, calcium stearate, talc, colloidal silica, synthetic aluminum silicate and magnesium aluminometasilicate (preferably talc), and (c) a plasticizer selected from the group consisting of acetyl tributyl citrate, acetyltriethyl citrate, castor oil, diacetylated monoglyceride, dibutyl sebacate, diethyl phthalate, glycerin, mono- and diacetylated monoglyceride, polyethylene glycol, propylene glycol, triacetin and triethyl citrate (preferably, triethyl citrate).

As the physiologically active substance, (1) (+)-6-(7-hydroxy-6,7-dihydro-5H-pyrrolo[1,2-c]imidazol-7-yl)-N-methyl-2-naphthamide or a salt thereof is preferably used.

The controlled release capsule of the present invention comprises the above-mentioned enteric granule and a fluidizer in a capsule.

As the fluidizer, for example, light anhydrous silicic acid, hydrated silicon dioxide, microcrystalline cellulose, synthetic aluminum silicate, titanium oxide, heavy anhydrous silicic acid, magnesium hydroxide-aluminum hydroxide coprecipitate, stearic acid, magnesium stearate, calcium stearate, tribasic calcium phosphate, talc, corn starch, magnesium aluminometasilicate, dibasic calcium phosphate fine granulated product and the like are used. Of these, light anhydrous silicic acid is preferable.

By adding a fluidizer, the enteric granule shows improved flowability and prevents electrification.

Moreover, the capsule may contain a lubricant such as magnesium stearate, calcium stearate, talc, colloidal silica, synthetic aluminum silicate, magnesium aluminometasilicate and the like, and the like.

Examples of the capsule include gelatin-capsule, hydroxypropylmethylcellulose•capsule and the like. Of these, hydroxypropylmethylcellulose•capsule size number 1 is preferable.

The controlled release capsule of the present invention can be produced by adding and mixing the above-mentioned enteric granule with a fluidizer and, where necessary, a lubricant and the like.

While the content of the fluidizer to be mixed with the enteric granule in the controlled release capsule preparation of the present invention varies depending on the content of the physiologically active substance, kind of the fluidizer, size of the preparation and the like, it is, for example, about 0.001 to about 10 wt %, preferably about 0.005 to about 1 wt %, more preferably about 0.01 to about 0.05 wt %.

While the content of the lubricant and the like to be mixed with the enteric granule in the controlled release capsule preparation of the present invention varies depending on the content of the physiologically active substance, kind of the lubricant etc., size of the preparation and the like, it is, for example, about 0.001 to about 10 wt %, preferably about 0.01 to about 1 wt %, more preferably about 0.05 to about 0.1 wt %.

In the controlled release capsule of the present invention, 1) according to Method 1 of the dissolution test in the Japanese Pharmacopoeia (rotating basket method, rotation speed 125 rpm, 37° C.) using 1000 mL of 0.1 mol/L hydrochloric acid, the dissolution rate of a physiologically active substance from a controlled release composition at 120 min after the start of the test is less than 10%, preferably less than 5%, more preferably less than 3%, and 2) according to Method 1 of the dissolution test in the Japanese Pharmacopoeia (rotating basket method, rotation speed 125 rpm, 37° C.) using a phosphate buffer (pH 7.2, 1000 mL) containing sodium dodecyl sulfate at 0.5%, the dissolution rate of a physiologically active substance from a controlled release composition at 45 min after the start of the test is not less than 70%, preferably not less than 80%, more preferably not less than 90%.

The film-coated controlled release capsule preparation of the present invention has low toxicity and few side effects, and thus can be safely administered orally to mammals (e.g., human, cow, horse, pig, dog, cat, monkey, mouse, rat, etc., and especially human). In particular, it can be used as a therapeutic and prophylactic medicine for the above-mentioned various diseases for which prophylactic and/or therapeutic effects can be obtained by inhibiting steroid $C_{17,20}$-lyase, and preferably for cancers such as prostate cancer, breast cancer or the like.

Dosage of the controlled release capsule preparation of the present invention varies depending on the kind of the physiologically active substance, the subject to be administered, the frequency of administration or the like, but the daily dosage in the case of, for example, oral administration to an adult patient having solid tumor (e.g., prostate cancer patient) is typically about 0.001 to about 500 mg/kg of body weight, preferably about 0.1 to about 40 mg/kg of body weight, and more preferably about 0.5 to about 20 mg/kg of body weight, as an effective amount of the physiologically active substance.

The controlled release capsule preparation of the present invention can have further enhanced effect when used in combination with physiologically active substances having different pharmaceutical effects. The physiologically active substance having different pharmaceutical effect may be preferably exemplified by the above-described combination drugs. The combination drugs can be used in different pharmaceutical compositions, or can be used in a mixed preparation prepared by adding them to the above-described controlled release capsule preparation.

The dosage of the combination drug can be appropriately selected on the basis of the quantities that are clinically used. Furthermore, the mixing ratio of the physiologically active substance and combination drug in the controlled release capsule preparation of the invention can be appropriately selected in accordance with the subject to be administered, disease to be treated, symptoms, combination or the like. For example, when the subject to be administered is a human, 0.01 to 100 parts by weight of a combination drug may be used with respect to 1 part by weight of the above-described physiologically active substance.

EXAMPLES

The following Examples further illustrate the present invention in detail, but they are mere examples and not to be construed to limit the scope thereof.

Also, (+)-6-(7-hydroxy-6,7-dihydro-5H-pyrrolo[1,2-c]imidazol-7-yl)-N-methyl-2-naphthamide (hereinafter, referred to as compound A) was used as the physiologically active substance in the following Examples.

Further, for hydroxypropylcellulose, microcrystalline cellulose and croscarmellose sodium, the products as specified in the 14$^{th}$ edition of the Japanese Pharmacopoeia were used.

Example 1

About 176 g of hydroxypropylmethylcellulose (TC-5-EW) was added to and dissolved in about 6072 mL of purified water. About 66 g of microcrystalline cellulose (PH10) was added and dispersed therein and about 176 g of low-substituted hydroxypropylcellulose (L-HPC-32W) was added and dispersed therein. About 1100 g of compound A was dispersed uniformly in the resulting polymer dispersion to yield a coating solution. About 720 g of Celphere CP-507 as the core particles was coated with about 7245 g of the above-prepared coating solution containing compound A, using a rotating blade fluidizing granulator (MP-10). The coating conditions were inlet air temperature of about 65° C., inlet air flow of about 1.8 m$^3$/min, spray pressure of about 0.3 MPa, spray air rate of about 100 Nl/hr, rotation speed of about 400 rpm, spray rate of about 30 g/min, and nozzle position on the lower side. The exhaustion humidity in the chamber was about 90% RH, and the product temperature was about 27° C. Adhesion of the coating solution to the nozzle was not observed. After completion of the coating operation, the granules were sieved through a 1180-μm sieve and the sieved granules were further sieved through a 710-μm sieve, and the remaining granules on the sieve were collected. The weight of the resulting granules (plain granule) was about 2010 g.

Then, about 59 g of triethyl citrate was dissolved in a mixture of about 7664 g of ethanol and about 852 mL of purified water, and about 444 g of Eudragit S100 and about 148 g of Eudragit L100 were respectively dissolved. About 296 g of talc was dispersed uniformly in the resulting polymer solution to yield a coating solution. About 1848 g of the above-mentioned granules (plain granules) were coated with about 9282 g of the polymer-containing coating solution prepared above using a rotating blade fluidizing granulator (MP-10). The coating conditions were inlet air temperature of about 50° C., inlet air flow of about 1.6 m$^3$/min, spray pressure of about 0.3 MPa, spray air rate of about 100 Nl/hr, rotation speed of about 250 rpm, spray rate of about 30 g/min, and nozzle position on the lower side. After completion of the coating operation, the granules were sieved through a 1400-μm sieve and the sieved granules were further sieved through a 850-μm sieve, and the remaining granules on the sieve were collected. The weight of the obtained granule (enteric granule) was about 2720 g, and the drug content was about 32 wt % of the granules.

About 2530 g of the obtained granules (enteric granules), about 2.0 g of talc and about 0.5 g of AEROSIL were mixed in a tumbler mixer (15 L) to give about 2520 g of mixed granules. The mixing conditions were rotation rate of about 30 rpm, and mixing time of about 2 min. Then, about 2439 g of the mixed granules was filled in a HPMC capsule No. 1 (about 540 g) using a capsule filling machine (Zanasi 6F), and the filled capsule was dried in vacuo at a shelf temperature of about 40° C. for about 16 hr to give a capsule (about 2570 g).

Example 2

In the same manner as in Example 1 except that the spray spray rate was about 20 g/min, plain granules were obtained. The exhaustion humidity in the chamber was about 70% RH, and the product temperature was about 30° C. Adhesion of the coating solution to the nozzle was not observed.

Example 3

About 176 g of hydroxypropylmethylcellulose (TC-5-EW) was added to and dissolved in about 6072 mL of purified water. About 66 g of microcrystalline cellulose (PH101) was added and dispersed therein and about 176 g of croscarmellose sodium (Ac-Di-Sol) was added and dispersed therein. About 1100 g of compound A was dispersed uniformly in the resulting polymer dispersion to yield a coating solution. About 720 g of Celphere CP-507 as the core particles was coated with about 7245 g of the above-prepared coating solution containing compound A, using a rotating blade fluidizing granulator (MP-10). The coating conditions were inlet air temperature of about 65° C., inlet air flow of about 1.8 m$^3$/min, spray pressure of about 0.5 MPa, spray air rate of about 100 Nl/hr, rotation speed of about 400 rpm, spray rate of about 30 g/min, and nozzle position on the lower side. The exhaustion humidity in the chamber was about 90% RH, and the product temperature was about 29° C. Adhesion of the coating solution to the nozzle was not observed. After completion of the coating operation, the granules were sieved through a 1180-μm sieve and the sieved granules were further sieved through a 710-μm sieve, and the granules remaining on the sieve were collected. The weight of the resulting granules (plain granule) was about 2000 g.

Example 4

In the same manner as in Example 3 except that the spray spray rate was about 20 g/min, plain granules were obtained. The exhaustion humidity in the chamber was about 70% RH, and the product temperature was about 32° C. Adhesion of the coating solution to the nozzle was not observed.

Example 5

About 176 g of hydroxypropylmethylcellulose (TC-5-EW) was added to and dissolved in about 6072 mL of purified water and about 242 g of microcrystalline cellulose (PH101) was added and dispersed therein. About 1100 g of compound A was dispersed uniformly in the resulting polymer dispersion to yield a coating solution. About 720 g of Celphere CP-507 as the core particles was coated with about 7245 g of the above-prepared coating solution containing compound A, using a rotating blade fluidizing granulator (MP-10). The coating conditions were inlet air temperature of about 65° C., inlet air flow of about 1.8 m$^3$/min, spray pressure of about 0.5 MPa, spray air rate of about 100 Nl/hr, rotation speed of about 400 rpm, spray rate of about 30 g/min, and nozzle position on the lower side. The exhaustion humidity in the chamber was about 90% RH, and the product temperature was about 30° C. Adhesion of the coating solution to the nozzle was not observed. After completion of the coating operation, the granules were sieved through a 1180-μm sieve and the sieved granules were further sieved through a 710-μm sieve, and the granules remaining on the sieve were collected. The weight of the resulting granules (plain granule) was about 2000 g.

Example 6

In the same manner as in Example 5 except that the spray spray rate was about 20 g/min, plain granules were obtained. The exhaustion humidity in the chamber was about 70% RH, and the product temperature was about 30° C. Adhesion of the coating solution to the nozzle was not observed.

Example 7

About 1232 g of hydroxypropylmethylcellulose (TC-5-EW) was added to and dissolved in about 42504 mL of purified water. About 462 g of microcrystalline cellulose (PH101) was added and dispersed therein and about 1232 g of low-substituted hydroxypropylcellulose (L-HPC-32) was added and dispersed therein. About 7700 g of compound A was dispersed uniformly in the resulting polymer dispersion to yield a coating solution. About 5040 g of Celphere CP-507 as the core particles was coated with about 52600 g of the above-prepared coating solution containing compound A, using a rotating blade fluidizing granulator (MP-25). The coating conditions were inlet air temperature of about 65° C., inlet air flow of about 10.8 m³/min, spray air rate of about 400 Nl/min, rotation speed of about 260 rpm, spray rate of about 120 g/min, and nozzle position on the lower side. Adhesion of the coating solution to the nozzle was not observed. After completion of the coating operation, the granules were sieved through a 1180-μm sieve and the sieved granules were further sieved through a 710-μm sieve, and the granules remaining on the sieve were collected. The weight of the resulting granules (plain granule) was about 14220 g.

Experimental Example 1

Dissolution Test (1)

Using 6 capsules obtained in Example 1, a dissolution test was performed. As a result, 1) in Method 1 of the dissolution test in the Japanese Pharmacopoeia (rotating basket method, rotation speed 125 rpm, 37° C.) using 1000 mL of 0.1 mol/L hydrochloric acid, the dissolution rate of compound A from the controlled release capsule at 120 min after the start of the test was 0% for all of 6 capsules, and 2) in Method 1 of the dissolution test in the Japanese Pharmacopoeia (rotating basket method, rotation speed 125 rpm, 37° C.) using a phosphate buffer (pH 7.2, 1000 mL) containing sodium dodecyl sulfate at 0.5%, the dissolution rate of compound A from the controlled release capsule at 45 min after the start of the test was within the range of 91 to 97% and the average value was 94%.

Experimental Example 2

Dissolution Test (2)

Using the plain granules obtained in Examples 1 to 6, a dissolution test was performed. As a result, in Method 1 of the dissolution test in the Japanese Pharmacopoeia (rotating basket method, rotation speed 50 rpm, 37° C.) using a phosphate buffer (pH 6.8, 900 mL) containing sodium dodecyl sulfate at 0.5%, the dissolution rate of compound A from the plain granule at 15 min after the start of the test was as shown in Table 1.

TABLE 1

| | dissolution rate (%) at 15 min later | |
|---|---|---|
| kind of disintegrant | apray rate of 20 g/min, (exhaustion humidity in the chamber of 70% RH) | apray rate of 30 g/min, (exhaustion humidity in the chamber of 90% RH) |
| low-substituted hydroxypropylcellulose (L-HPC-32) | 65.1 | 49.7 |
| croscarmellose sodium (Ac-Di-Sol) | 63.4 | 66.6 |
| microcrystalline cellulose | 41.0 | 40.9 |

From the results, it has been clarified that the dissolution property of the physiologically active substance from the plain granules is not influenced by the production time (exhaustion humidity in the chamber) due to the use of croscarmellose sodium and/or microcrystalline cellulose as a disintegrant, and the production time can be increased.

Reference Example 1

Production of 6-(7-hydroxy-6,7-dihydro-5H-pyrrolo[1,2-c]imidazol-7-yl)-N-methyl-2-naphthamide

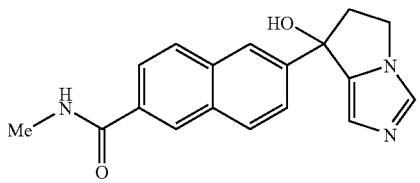 [SMILES: CNC(=O)c1ccc2cc(C3(O)CCn4cncc43)ccc2c1]

Under an argon atmosphere, dry THF (150 ml) was dry cooled to −65° C. in a dry ice-acetone bath, and a solution (1.6M: 45.2 ml) of n-butyllithium in hexane was added. To this solution was added a solution (cooled to 10° C.) of 6-bromo-N-methyl-2-naphthamide (8.68 g) in dry THF (700 ml) at −55° C. or below, and the mixture was stirred for 1 hr. Then, a solution of 5,6-dihydro-7H-pyrrolo[1,2-c]imidazol-7-one (3.65 g) in dry THF (60 ml) was added dropwise. After stirring at the same temperature for 1.5 hr, saturated aqueous ammonium chloride (120 ml) was added to quench the reaction. Under reduced pressure, the solvent was evaporated, an ethanol-soluble product was extracted from the obtained residue and the solvent was evaporated again. The residue was purified by flash silica gel column chromatography (eluate, chloroform/7%-ammonia-containing methanol; 19/1→9/1). The eluate was recrystallized from methanol to give the title compound (3.36 g) as colorless crystals.

$^1$H-NMR (CDCl$_3$+CD$_3$OD) δ: 2.89-3.02 (2H, m), 3.04 (3H, s), 4.12-4.25 (1H, m), 4.27-4.43 (1H, m), 6.79 (1H, s), 7.20 (1H, q, J=4.6 Hz), 7.54 (1H, s), 7.63 (1H, dd, J=1.8 Hz, 8.6 Hz), 7.83 (2H, s), 7.89 (1H, d, J=8.6 Hz), 8.03 (1H, s), 8.28 (1H, s). IR (KBr): 3500-3000, 1644, 1605, 1559, 1497, 1464, 1318, 1082 cm−1.

Reference Example 2

Production of (+)-6-(7-hydroxy-6,7-dihydro-5H-pyrrolo[1,2-c]imidazol-7-yl)-N-methyl-2-naphthamide 6-(7-Hydroxy-6,7-dihydro-5H-pyrrolo[1,2-c]imidazole-7-yl)-N-methyl-2-naphthamide obtained in Reference Example 1 was applied to chromatography (eluate: hexane-ethanol=1:1) using an optical isomer separation column (CHIRALPAK AD: manufactured by DAICEL CHEMICAL INDUSTRIES, LTD.). As a second elution fraction, (+)-6-(7-hydroxy-6,7-dihydro-5H-pyrrolo[1,2-c]imidazol-7-yl)-N- methyl-2-naphthamide was obtained. Enantiomer excess>99% ee [α]$D^{20}$+83.1° (C=0.997, methanol)

Reference Example 3

Production of 6-(7-hydroxy-6,7-dihydro-5H-pyrrolo[1,2-c]imidazol-7-yl)-2-naphthamide

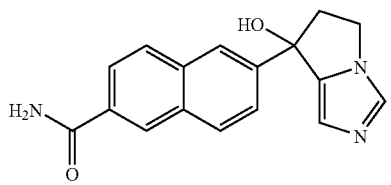 [SMILES: NC(=O)c1ccc2cc(C3(O)CCn4cncc43)ccc2c1]

(i) Production of 6-(7-hydroxy-6,7-dihydro-5H-pyrrolo[1,2-c]imidazol-7-yl)-2-naphthoic acid 6-Bromo-2-naphthoic acid (1.51 g) was dissolved in dry THF (50 ml), and cooled to −100° C. in a liquid nitrogen/diethyl ether bath. Under stirring a solution (1.6M; 7.88 ml) of n-butyllithium in hexane was added dropwise at −95° C. or below over 5 min. After stirring at −100° C. for 30 min and at −80° C. for 10 min, the mixture was cooled to −100° C. again. A solution of 5,6-dihydro-7H-pyrrolo[1,2-c]imidazol-7-one (0.61 g) in dry THF (11 ml) was added dropwise at −90° C. or below over 5 min. After stirring at the same temperature for 30 min, the temperature was raised to −70° C. over 30 min, and saturated aqueous ammonium chloride solution (25 ml) was added to quench the reaction. After stirring for 10 min, ethyl acetate (50 ml) was added to partition the solution. The organic layer was removed and the aqueous layer was concentrated to dryness. The obtained residue was purified by flash column chromatography, and the object fraction was dissolved in methanol. This solution was concentrated, ether was added to the precipitated powder and the powder was collected by filtration and dried. The title compound (180 mg) was obtained as a colorless powder. The mother liquor was concentrated to give a residue (449 mg) containing the title compound.

$^1$H-NMR (CD$_3$OD) δ; 2.87-3.13 (2H, m), 4.28-4.50 (2H, m), 6.94 (1H, s), 7.65 (1H, dd, J=1.6 Hz, 8.6 Hz), 7.90 (1H, d, J=8.4 Hz), 7.99 (1H, d, J=8.6 Hz), 8.01 (1H, s), 8.06 (1H, dd, J=1.4 Hz, 8.4 Hz), 8.09 (1H, s), 8.57 (1H, s).

IR (KBr): 3500-3000, 1698, 1609, 1551, 1480, 1397, 1325, 1086 cm$^{-1}$.

FAB-Mass: 295 (MH$^+$)

(ii) Production of 6-(7-hydroxy-6,7-dihydro-5H-pyrrolo[1,2-c]imidazol-7-yl)-2-naphthamide 6-(7-Hydroxy-6,7-dihydro-5H-pyrrolo[1,2-c]imidazole-7-yl)-2-naphthoic acid (449 mg), 1-ethyl-3-(3-dimethylaminopropyl)carbodiimide•hydrochloride (321 mg) and 1-hydroxy-1H-benzotriazole•monohydrate (301 mg) were dissolved in DMF (7.6 ml), and diisopropylethylamine (216 mg) was added with stirring under ice cooling. The mixture was allowed to warm to room temperature and stirred for 18 hr. Silica gel (3 g) was added to the reaction mixture and the mixture was concentrated under reduced pressure to dryness. The obtained residue was purified by silica gel column chromatography (developing solution: chloroform/7% aqueous ammonia-containing methanol:19/1). The eluate was concentrated to dryness, and the residue was recrystallized from ethanol to give the title compound (53 mg).

$^1$H-NMR (CDCl$_3$+CD$_3$OD) δ; 2.94-3.00 (2H, m), 4.15-4.40 (2H, m), 6.82 (1H, s), 7.58 (1H, s), 7.66 (1H, dd, J=1.8 Hz, 8.6 Hz), 7.90 (2H, s), 7.95 (1H, d, J=8.6 Hz), 8.07 (1H, s), 8.40 (1H, s).

IR (KBr): 3345, 1663, 1618, 1599, 1493, 1414, 1080 cm$^{-1}$.

elemental analysis: Calculated; C$_{17}$H$_{15}$N$_3$O$_2$.H$_2$O; C, 65.58; H, 5.50; N, 13.50.

Found; C, 65.63; H, 5.50; N, 13.73.

Reference Example 4

Production of (+)-6-(7-hydroxy-6,7-dihydro-5H-pyrrolo[1,2-c]imidazol-7-yl)-2-naphthamide and (−)-6-(7-hydroxy-6,7-dihydro-5H-pyrrolo[1,2-c]imidazol-7-yl)-2-naphthamide In the same manner as in Reference Example 2, by applying 6-(7-hydroxy-6,7-dihydro-5H-pyrrolo[1,2-c]imidazol-7-yl)-2-naphthamide obtained in Reference Example 3 to chromatography. (eluate:hexane-ethanol=1:1) using an optical isomer separation column (CHIRALPAK AD: manufactured by DAICEL CHEMICAL INDUSTRIES, LTD.), (+)-6-(7-hydroxy-6,7-dihydro-5H-pyrrolo[1,2-c]imidazol-7-yl)-2-naphthamide and, (−)-6-(7-hydroxy-6,7-dihydro-5H-pyrrolo[1,2-c]imidazol-7-yl)-2-naphthamide can be obtained.

INDUSTRIAL APPLICABILITY

According to the present invention, a controlled release capsule preparation for oral administration of an imidazole derivative, which has steroid C$_{17,20}$-lyase inhibiting activity and which has remarkably improved sustainability of the blood concentration, is provided.

This application is based on a patent application No. 2005-059501 filed in Japan, the contents of which are incorporated in full herein by this reference.

The invention claimed is:

1. A controlled release capsule preparation for oral administration, which comprises (i) an enteric granule comprising a plain granule wherein a core particle is coated with a coating layer comprising
   (1) a physiologically active substance which is (+)-6-(7-hydroxy-6,7-dihydro-5H-pyrrolo[1,2-c]imidazol-7-yl)-N-methyl-2-naphthamide or a salt thereof,
   (2) a hydrophilic polymer which is hydroxypropylmethylcellulose,
   (3) an excipient which is microcrystalline cellulose,
   (4) a disintegrant which is croscarmellose sodium,
   (5) (a) an enteric coating agent which is methacrylic acid copolymers,
      (b) a lubricant which is talc, and
      (c) a plasticizer which is triethyl citrate,
   (ii) a fluidizer which is light anhydrous silicic acid, and
   (iii) a lubricant which is talc.

* * * * *